United States Patent [19]

Horwitz

[11] Patent Number: 5,770,561
[45] Date of Patent: Jun. 23, 1998

[54] METHOD FOR POTENTIATING BPI PROTEIN PRODUCT BACTERICIDAL ACTIVITY BY ADMINISTRATION OF LBP PROTEIN PRODUCTS

[75] Inventor: Arnold Horwitz, Los Angeles, Calif.

[73] Assignee: Xoma Corporation, Berkeley, Calif.

[21] Appl. No.: 274,303

[22] Filed: Jul. 11, 1994

Related U.S. Application Data

[63] Continuation-in-part of Ser. No. 93,201, Jul. 14, 1993, abandoned.

[51] Int. Cl.[6] .......................... A61K 38/16; A61K 38/14
[52] U.S. Cl. .................................. 514/8; 514/12; 514/21
[58] Field of Search ..................... 514/8, 12, 21

[56] References Cited

U.S. PATENT DOCUMENTS

| | | | |
|---|---|---|---|
| 5,089,274 | 2/1992 | Marra et al. | 514/21 |
| 5,171,739 | 12/1992 | Scott | 514/12 |
| 5,198,541 | 3/1993 | Elsbach et al. | 435/69.1 |
| 5,234,912 | 8/1993 | Marra et al. | 514/21 |
| 5,308,834 | 5/1994 | Scott et al. | 514/12 |
| 5,334,584 | 8/1994 | Scott et al. | 514/12 |
| 5,348,942 | 9/1994 | Little, II et al. | 514/12 |

FOREIGN PATENT DOCUMENTS

| | | |
|---|---|---|
| WO 92/03535 | 3/1992 | WIPO . |
| WO 92/09621 | 6/1992 | WIPO . |
| WO 93/06228 | 4/1993 | WIPO . |
| WO 93/23434 | 11/1993 | WIPO . |
| WO 93/23540 | 11/1993 | WIPO . |
| WO 94/17819 | 8/1994 | WIPO . |
| WO 94/18323 | 8/1994 | WIPO . |
| WO 94/20128 | 9/1994 | WIPO . |
| WO 94/20129 | 9/1994 | WIPO . |
| WO 94/20532 | 9/1994 | WIPO . |

OTHER PUBLICATIONS

Elsbach et al., "Separation and Purification of a Potent Bactericidal/Permeability–Increasing Protein and a Closely Associated Phospholipase A$_2$ from Rabbit Polymorphonuclear Leukocytes", *J. Biol. Chem.*, 254(21):11000–11009 (Nov. 10, 1979).

Elsbach and Weiss, "Oxygen–Independent Antimicrobial Systems of Phagocytes", *Inflammation: Basic Principles and Clinical Correlates*, eds. Gallin et al., Chapter 30, Review Press, Ltd. (1992).

Gazzano–Santoro et al., "High–Affinity Binding of the Bactericidal/Permeability–Increasing Protein and a Recombinant Amino–Terminal Fragment to the Lipid A Region of Lipopolysaccharide", *Infect. Immun.*, 60(11):4754–4761 (Nov. 1992).

Gray et al., "Cloning of the cDNA of a Human Neutrophil Bactericidal Protein", *J. Biol. Chem.*, 264(16):9505–9509 (Jun. 5, 1989).

Levy et al., "Antibacterial 15–kDa Protein Isoforms (p15s) Are Members of a Novel Family of Leukocyte Proteins", *J. Biol. Chem.*, 268(8):6058–6068 (Mar. 16, 1993).

Mannion et al., "Preferential Binding of the Neutrophil Cytoplasmic Granule–Derived Bactericidal/Permeability Increasing Protein to Target Bacteria", *J. Clin. Invest.*, 142(8):2807–2812 (Apr. 15, 1989).

Mannion et al., "Separation of Sublethal and Lethal Effects of the Bactericidal/Permeability Increasing Protein on *Escheria coli*", *J. Clin. Invest.*, 85:853–860 (Mar. 1990).

Mannion et al., "Separation of Sublethal and Lethal Effects of Polymorphonuclear Leukocytes on *Escheria coli*", *J. Clin. Invest.*, 86:631–641 (Aug. 1990).

Marra et al., "The Role of Bactericidal/Permeability–Increasing Protein as a Natural Inhibitor of Bacterial Endotoxin", *J. Immunol.* 148(2):532–537 (Jan. 15, 1992).

(List continued on next page.)

*Primary Examiner*—Ponnathapura Achutamurthy
*Attorney, Agent, or Firm*—Marshall, O'Toole, Gerstein, Murray & Borun

[57] ABSTRACT

The present invention provides methods of potentiating the gram-negative bactericidal activity of BPI protein products by means of administering LBP protein products.

21 Claims, 18 Drawing Sheets

OTHER PUBLICATIONS

Ooi et al., "Endotoxin–neutralizing Properties of the 25 kD N–Terminal Fragment and a Newly Isolated 30 kD C–Terminal Fragment of the 55–60 kD Bactericidal/Permeability–increasing Protein of Human Neutrophils", *J. Exp. Med.*, 174:649–655 (Sep. 1991).

Ooi et al., "A 25–kDa $NH_2$–terminal Fragment Carries all the Antibacterial Activities of the Human Neutrophil 60–kDa Bactericidal/Permeability–increasing Protein", *J. Biol. Chem.*, 262(31):1481–14894 (1987).

Schumann et al., "Structure and Function of Lipopolysaccharide Binding Protein", *Science*, 249:1429–1431 (Sep. 21, 1990).

Tobias et al., "Participation of Lipopolysaccharide–binding Protein in Lipopolysaccharide–dependant Macrophage Activation", *Am. J. Resp. Cell. Mol. Biol.*, 7:239–245 (1992).

Ulevitch et al., "A New Model of Macrophage Stimulation by Bacterial Lipopolysaccharide", *Advances in Understanding Trauma and Burn Injury*, 30(12):S189–S192 (Dec. 1990).

Weiss et al., "Resistance of Gram–negative Bacteria to Purified Bactericidal Leukocyte Proteins", *J. Clin. Invest.* 65:619–628 (Mar. 1980).

Weiss et al., "Cellular and Subcellular Localization of the Bactericidal/Permeability–Increasing Protein of Neutrophils", *Blood*, 69(2):652–659 (Feb. 1987).

Weiss et al., "Human Bactericidal,Permeability–increasing Protein and a Recombinant $NH_2$–Terminal Fragment Cause Killing of Serum–resistant Gram–negative Bacteria in Whole Blood and Inhibit Tumor Necrosis Factor Release Induced by the Bacteria", *J. Clin. Invest.*, 90:1122–1130 (Sep. 1992).

Wright et al., "CD14, a Receptor for Complexes of Lipopolysaccharide (LPS) and LPS Binding Protein", *Science*, 249:1431–1433 (Sep. 21, 1990).

Heumann et al., "Competition between Bactericidal/Permeability–Increasing Protein and Lipopolysaccharide–Binding Protein for Lipopolysaccharide Binding to Monocytes", *J. Infectious Diseases*, 167(6):1351–1357 (Jun. 1993).

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 1813 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 31..1491

( i x ) FEATURE:
        ( A ) NAME/KEY: mat_peptide
        ( B ) LOCATION: 124..1491

( i x ) FEATURE:
        ( A ) NAME/KEY: misc_feature
        ( D ) OTHER INFORMATION: "rBPI"

( x i ) SEQUENCE DESCRIPTION: SEQ ID NO:1:

```
CAGGCCTTGA GGTTTTGGCA GCTCTGGAGG ATG AGA GAG AAC ATG GCC AGG GGC        54
                                 Met Arg Glu Asn Met Ala Arg Gly
                                 -31 -30                     -25

CCT TGC AAC GCG CCG AGA TGG GTG TCC CTG ATG GTG CTC GTC GCC ATA        102
Pro Cys Asn Ala Pro Arg Trp Val Ser Leu Met Val Leu Val Ala Ile
            -20             -15                     -10

GGC ACC GCC GTG ACA GCG GCC GTC AAC CCT GGC GTC GTG GTC AGG ATC        150
Gly Thr Ala Val Thr Ala Ala Val Asn Pro Gly Val Val Val Arg Ile
         -5                   1               5

TCC CAG AAG GGC CTG GAC TAC GCC AGC CAG CAG GGG ACG GCC GCT CTG        198
Ser Gln Lys Gly Leu Asp Tyr Ala Ser Gln Gln Gly Thr Ala Ala Leu
 10              15                  20                      25

CAG AAG GAG CTG AAG AGG ATC AAG ATT CCT GAC TAC TCA GAC AGC TTT        246
Gln Lys Glu Leu Lys Arg Ile Lys Ile Pro Asp Tyr Ser Asp Ser Phe
             30              35                      40

AAG ATC AAG CAT CTT GGG AAG GGG CAT TAT AGC TTC TAC AGC ATG GAC        294
Lys Ile Lys His Leu Gly Lys Gly His Tyr Ser Phe Tyr Ser Met Asp
             45              50                      55

ATC CGT GAA TTC CAG CTT CCC AGT TCC CAG ATA AGC ATG GTG CCC AAT        342
Ile Arg Glu Phe Gln Leu Pro Ser Ser Gln Ile Ser Met Val Pro Asn
         60                  65                  70

GTG GGC CTT AAG TTC TCC ATC AGC AAC GCC AAT ATC AAG ATC AGC GGG        390
Val Gly Leu Lys Phe Ser Ile Ser Asn Ala Asn Ile Lys Ile Ser Gly
         75                  80                  85

AAA TGG AAG GCA CAA AAG AGA TTC TTA AAA ATG AGC GGC AAT TTT GAC        438
Lys Trp Lys Ala Gln Lys Arg Phe Leu Lys Met Ser Gly Asn Phe Asp
 90              95                  100                     105

CTG AGC ATA GAA GGC ATG TCC ATT TCG GCT GAT CTG AAG CTG GGC AGT        486
Leu Ser Ile Glu Gly Met Ser Ile Ser Ala Asp Leu Lys Leu Gly Ser
                     110                 115                 120

AAC CCC ACG TCA GGC AAG CCC ACC ATC ACC TGC TCC AGC TGC AGC AGC        534
Asn Pro Thr Ser Gly Lys Pro Thr Ile Thr Cys Ser Ser Cys Ser Ser
             125                 130                 135

CAC ATC AAC AGT GTC CAC GTG CAC ATC TCA AAG AGC AAA GTC GGG TGG        582
His Ile Asn Ser Val His Val His Ile Ser Lys Ser Lys Val Gly Trp
             140                 145                 150

CTG ATC CAA CTC TTC CAC AAA AAA ATT GAG TCT GCG CTT CGA AAC AAG        630
Leu Ile Gln Leu Phe His Lys Lys Ile Glu Ser Ala Leu Arg Asn Lys
 155                 160                 165

ATG AAC AGC CAG GTC TGC GAG AAA GTG ACC AAT TCT GTA TCC TCC AAG        678
Met Asn Ser Gln Val Cys Glu Lys Val Thr Asn Ser Val Ser Ser Lys
170                 175                 180                 185
```

| | | | | | | | | | | | | | | | | |
|---|---|---|---|---|---|---|---|---|---|---|---|---|---|---|---|---|
| CTG | CAA | CCT | TAT | TTC | CAG | ACT | CTG | CCA | GTA | ATG | ACC | AAA | ATA | GAT | TCT | 726 |
| Leu | Gln | Pro | Tyr 190 | Phe | Gln | Thr | Leu | Pro 195 | Val | Met | Thr | Lys | Ile | Asp 200 | Ser | |
| GTG | GCT | GGA | ATC | AAC | TAT | GGT | CTG | GTG | GCA | CCT | CCA | GCA | ACC | ACG | GCT | 774 |
| Val | Ala | Gly | Ile 205 | Asn | Tyr | Gly | Leu | Val 210 | Ala | Pro | Pro | Ala | Thr | Thr 215 | Ala | |
| GAG | ACC | CTG | GAT | GTA | CAG | ATG | AAG | GGG | GAG | TTT | TAC | AGT | GAG | AAC | CAC | 822 |
| Glu | Thr | Leu | Asp 220 | Val | Gln | Met | Lys | Gly 225 | Glu | Phe | Tyr | Ser | Glu | Asn 230 | His | |
| CAC | AAT | CCA | CCT | CCC | TTT | GCT | CCA | CCA | GTG | ATG | GAG | TTT | CCC | GCT | GCC | 870 |
| His | Asn 235 | Pro | Pro | Pro | Phe | Ala 240 | Pro | Pro | Val | Met | Glu 245 | Phe | Pro | Ala | Ala | |
| CAT | GAC | CGC | ATG | GTA | TAC | CTG | GGC | CTC | TCA | GAC | TAC | TTC | TTC | AAC | ACA | 918 |
| His Asp 250 | | Arg | Met | Val | Tyr 255 | Leu | Gly | Leu | Ser | Asp 260 | Tyr | Phe | Phe | Asn | Thr 265 | |
| GCC | GGG | CTT | GTA | TAC | CAA | GAG | GCT | GGG | GTC | TTG | AAG | ATG | ACC | CTT | AGA | 966 |
| Ala | Gly | Leu | Val | Tyr 270 | Gln | Glu | Ala | Gly | Val 275 | Leu | Lys | Met | Thr | Leu 280 | Arg | |
| GAT | GAC | ATG | ATT | CCA | AAG | GAG | TCC | AAA | TTT | CGA | CTG | ACA | ACC | AAG | TTC | 1014 |
| Asp | Asp | Met | Ile 285 | Pro | Lys | Glu | Ser | Lys 290 | Phe | Arg | Leu | Thr | Thr | Lys 295 | Phe | |
| TTT | GGA | ACC | TTC | CTA | CCT | GAG | GTG | GCC | AAG | AAG | TTT | CCC | AAC | ATG | AAG | 1062 |
| Phe | Gly | Thr 300 | Phe | Leu | Pro | Glu | Val 305 | Ala | Lys | Lys | Phe | Pro 310 | Asn | Met | Lys | |
| ATA | CAG | ATC | CAT | GTC | TCA | GCC | TCC | ACC | CCG | CCA | CAC | CTG | TCT | GTG | CAG | 1110 |
| Ile | Gln 315 | Ile | His | Val | Ser | Ala 320 | Ser | Thr | Pro | Pro | His 325 | Leu | Ser | Val | Gln | |
| CCC | ACC | GGC | CTT | ACC | TTC | TAC | CCT | GCC | GTG | GAT | GTC | CAG | GCC | TTT | GCC | 1158 |
| Pro Thr 330 | | Gly | Leu | Thr | Phe 335 | Tyr | Pro | Ala | Val | Asp 340 | Val | Gln | Ala | Phe | Ala 345 | |
| GTC | CTC | CCC | AAC | TCC | TCC | CTG | GCT | TCC | CTC | TTC | CTG | ATT | GGC | ATG | CAC | 1206 |
| Val | Leu | Pro | Asn | Ser 350 | Ser | Leu | Ala | Ser | Leu 355 | Phe | Leu | Ile | Gly | Met 360 | His | |
| ACA | ACT | GGT | TCC | ATG | GAG | GTC | AGC | GCC | GAG | TCC | AAC | AGG | CTT | GTT | GGA | 1254 |
| Thr | Thr | Gly | Ser 365 | Met | Glu | Val | Ser | Ala 370 | Glu | Ser | Asn | Arg | Leu | Val 375 | Gly | |
| GAG | CTC | AAG | CTG | GAT | AGG | CTG | CTC | CTG | GAA | CTG | AAG | CAC | TCA | AAT | ATT | 1302 |
| Glu | Leu | Lys 380 | Leu | Asp | Arg | Leu | Leu 385 | Leu | Glu | Leu | Lys | His 390 | Ser | Asn | Ile | |
| GGC | CCC | TTC | CCG | GTT | GAA | TTG | CTG | CAG | GAT | ATC | ATG | AAC | TAC | ATT | GTA | 1350 |
| Gly | Pro | Phe 395 | Pro | Val | Glu | Leu | Leu 400 | Gln | Asp | Ile | Met | Asn 405 | Tyr | Ile | Val | |
| CCC | ATT | CTT | GTG | CTG | CCC | AGG | GTT | AAC | GAG | AAA | CTA | CAG | AAA | GGC | TTC | 1398 |
| Pro 410 | Ile | Leu | Val | Leu | Pro 415 | Arg | Val | Asn | Glu | Lys 420 | Leu | Gln | Lys | Gly | Phe 425 | |
| CCT | CTC | CCG | ACG | CCG | GCC | AGA | GTC | CAG | CTC | TAC | AAC | GTA | GTG | CTT | CAG | 1446 |
| Pro | Leu | Pro | Thr | Pro 430 | Ala | Arg | Val | Gln | Leu 435 | Tyr | Asn | Val | Val | Leu 440 | Gln | |
| CCT | CAC | CAG | AAC | TTC | CTG | CTG | TTC | GGT | GCA | GAC | GTT | GTC | TAT | AAA | | 1491 |
| Pro | His | Gln | Asn 445 | Phe | Leu | Leu | Phe | Gly 450 | Ala | Asp | Val | Val | Tyr 455 | Lys | | |

| | | | | | |
|---|---|---|---|---|---|
| TGAAGGCACC | AGGGGTGCCG | GGGGCTGTCA | GCCGCACCTG | TTCCTGATGG | GCTGTGGGGC | 1551 |
| ACCGGCTGCC | TTTCCCCAGG | GAATCCTCTC | CAGATCTTAA | CCAAGAGCCC | CTTGCAAACT | 1611 |
| TCTTCGACTC | AGATTCAGAA | ATGATCTAAA | CACGAGGAAA | CATTATTCAT | TGGAAAAGTG | 1671 |
| CATGGTGTGT | ATTTTAGGGA | TTATGAGCTT | CTTTCAAGGG | CTAAGGCTGC | AGAGATATTT | 1731 |
| CCTCCAGGAA | TCGTGTTTCA | ATTGTAACCA | AGAAATTTCC | ATTTGTGCTT | CATGAAAAAA | 1791 |
| AACTTCTGGT | TTTTTTCATG | TG | | | | 1813 |

( 2 ) INFORMATION FOR SEQ ID NO:2:

( i ) SEQUENCE CHARACTERISTICS:
        ( A ) LENGTH: 487 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Arg  Glu  Asn  Met  Ala  Arg  Gly  Pro  Cys  Asn  Ala  Pro  Arg  Trp  Val
-31  -30                      -25                      -20

Ser  Leu  Met  Val  Leu  Val  Ala  Ile  Gly  Thr  Ala  Val  Thr  Ala  Ala  Val
-15                      -10                      -5                           1

Asn  Pro  Gly  Val  Val  Val  Arg  Ile  Ser  Gln  Lys  Gly  Leu  Asp  Tyr  Ala
                 5                       10                      15

Ser  Gln  Gln  Gly  Thr  Ala  Ala  Leu  Gln  Lys  Glu  Leu  Lys  Arg  Ile  Lys
          20                        25                      30

Ile  Pro  Asp  Tyr  Ser  Asp  Ser  Phe  Lys  Ile  Lys  His  Leu  Gly  Lys  Gly
          35                   40                       45

His  Tyr  Ser  Phe  Tyr  Ser  Met  Asp  Ile  Arg  Glu  Phe  Gln  Leu  Pro  Ser
50                        55                       60                        65

Ser  Gln  Ile  Ser  Met  Val  Pro  Asn  Val  Gly  Leu  Lys  Phe  Ser  Ile  Ser
                 70                       75                        80

Asn  Ala  Asn  Ile  Lys  Ile  Ser  Gly  Lys  Trp  Lys  Ala  Gln  Lys  Arg  Phe
                 85                       90                       95

Leu  Lys  Met  Ser  Gly  Asn  Phe  Asp  Leu  Ser  Ile  Glu  Gly  Met  Ser  Ile
          100                       105                      110

Ser  Ala  Asp  Leu  Lys  Leu  Gly  Ser  Asn  Pro  Thr  Ser  Gly  Lys  Pro  Thr
     115                        120                      125

Ile  Thr  Cys  Ser  Ser  Cys  Ser  Ser  His  Ile  Asn  Ser  Val  His  Val  His
130                        135                      140                     145

Ile  Ser  Lys  Ser  Lys  Val  Gly  Trp  Leu  Ile  Gln  Leu  Phe  His  Lys  Lys
                 150                      155                           160

Ile  Glu  Ser  Ala  Leu  Arg  Asn  Lys  Met  Asn  Ser  Gln  Val  Cys  Glu  Lys
          165                       170                      175

Val  Thr  Asn  Ser  Val  Ser  Ser  Lys  Leu  Gln  Pro  Tyr  Phe  Gln  Thr  Leu
          180                       185                      190

Pro  Val  Met  Thr  Lys  Ile  Asp  Ser  Val  Ala  Gly  Ile  Asn  Tyr  Gly  Leu
     195                       200                      205

Val  Ala  Pro  Pro  Ala  Thr  Thr  Ala  Glu  Thr  Leu  Asp  Val  Gln  Met  Lys
210                        215                      220                     225

Gly  Glu  Phe  Tyr  Ser  Glu  Asn  His  His  Asn  Pro  Pro  Pro  Phe  Ala  Pro
                 230                      235                           240

Pro  Val  Met  Glu  Phe  Pro  Ala  Ala  His  Asp  Arg  Met  Val  Tyr  Leu  Gly
          245                       250                      255

Leu  Ser  Asp  Tyr  Phe  Phe  Asn  Thr  Ala  Gly  Leu  Val  Tyr  Gln  Glu  Ala
          260                       265                      270

Gly  Val  Leu  Lys  Met  Thr  Leu  Arg  Asp  Asp  Met  Ile  Pro  Lys  Glu  Ser
     275                       280                      285

Lys  Phe  Arg  Leu  Thr  Thr  Lys  Phe  Phe  Gly  Thr  Phe  Leu  Pro  Glu  Val
290                        295                      300                     305

Ala  Lys  Lys  Phe  Pro  Asn  Met  Lys  Ile  Gln  Ile  His  Val  Ser  Ala  Ser
                 310                      315                           320

Thr  Pro  Pro  His  Leu  Ser  Val  Gln  Pro  Thr  Gly  Leu  Thr  Phe  Tyr  Pro
```

|     |     |     |     |     | 325 |     |     |     |     | 330 |     |     |     |     | 335 |     |     |
|-----|-----|-----|-----|-----|-----|-----|-----|-----|-----|-----|-----|-----|-----|-----|-----|-----|-----|
| Ala | Val | Asp | Val | Gln | Ala | Phe | Ala | Val | Leu | Pro | Asn | Ser | Ser | Leu | Ala |
|     |     | 340 |     |     |     |     | 345 |     |     |     |     | 350 |     |     |     |
| Ser | Leu | Phe | Leu | Ile | Gly | Met | His | Thr | Thr | Gly | Ser | Met | Glu | Val | Ser |
|     | 355 |     |     |     |     | 360 |     |     |     |     | 365 |     |     |     |     |
| Ala | Glu | Ser | Asn | Arg | Leu | Val | Gly | Glu | Leu | Lys | Leu | Asp | Arg | Leu | Leu |
| 370 |     |     |     |     | 375 |     |     |     |     | 380 |     |     |     |     | 385 |
| Leu | Glu | Leu | Lys | His | Ser | Asn | Ile | Gly | Pro | Phe | Pro | Val | Glu | Leu | Leu |
|     |     |     |     | 390 |     |     |     |     | 395 |     |     |     |     | 400 |     |
| Gln | Asp | Ile | Met | Asn | Tyr | Ile | Val | Pro | Ile | Leu | Val | Leu | Pro | Arg | Val |
|     |     |     | 405 |     |     |     |     | 410 |     |     |     |     | 415 |     |     |
| Asn | Glu | Lys | Leu | Gln | Lys | Gly | Phe | Pro | Leu | Pro | Thr | Pro | Ala | Arg | Val |
|     |     | 420 |     |     |     |     | 425 |     |     |     |     | 430 |     |     |     |
| Gln | Leu | Tyr | Asn | Val | Val | Leu | Gln | Pro | His | Gln | Asn | Phe | Leu | Leu | Phe |
|     |     | 435 |     |     |     |     | 440 |     |     |     |     | 445 |     |     |     |
| Gly | Ala | Asp | Val | Val | Tyr | Lys |     |     |     |     |     |     |     |     |     |
| 450 |     |     |     |     | 455 |     |     |     |     |     |     |     |     |     |     |

( 2 ) INFORMATION FOR SEQ ID NO:3:

( i ) SEQUENCE CHARACTERISTICS:
        ( A ) LENGTH: 591 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS
        ( B ) LOCATION: 1..591

( i x ) FEATURE:
        ( A ) NAME/KEY: misc_feature
        ( D ) OTHER INFORMATION: "rLBP25"

( x i ) SEQUENCE DESCRIPTION: SEQ ID NO:3:

| GCC | AAC | CCC | GGC | TTG | GTC | GCC | AGG | ATC | ACC | GAC | AAG | GGA | CTG | CAG | TAT | 48 |
|-----|-----|-----|-----|-----|-----|-----|-----|-----|-----|-----|-----|-----|-----|-----|-----|----|
| Ala | Asn | Pro | Gly | Leu | Val | Ala | Arg | Ile | Thr | Asp | Lys | Gly | Leu | Gln | Tyr |    |
| 1   |     |     |     | 5   |     |     |     |     | 10  |     |     |     |     | 15  |     |    |
| GCG | GCC | CAG | GAG | GGG | CTA | TTG | GCT | CTG | CAG | AGT | GAG | CTG | CTC | AGG | ATC | 96 |
| Ala | Ala | Gln | Glu | Gly | Leu | Leu | Ala | Leu | Gln | Ser | Glu | Leu | Leu | Arg | Ile |    |
|     |     |     | 20  |     |     |     |     | 25  |     |     |     |     | 30  |     |     |    |
| ACG | CTG | CCT | GAC | TTC | ACC | GGG | GAC | TTG | AGG | ATC | CCC | CAC | GTC | GGC | CGT | 144 |
| Thr | Leu | Pro | Asp | Phe | Thr | Gly | Asp | Leu | Arg | Ile | Pro | His | Val | Gly | Arg |    |
|     |     | 35  |     |     |     |     | 40  |     |     |     |     | 45  |     |     |     |    |
| GGG | CGC | TAT | GAG | TTC | CAC | AGC | CTG | AAC | ATC | CAC | AGC | TGT | GAG | CTG | CTT | 192 |
| Gly | Arg | Tyr | Glu | Phe | His | Ser | Leu | Asn | Ile | His | Ser | Cys | Glu | Leu | Leu |    |
|     | 50  |     |     |     |     | 55  |     |     |     |     | 60  |     |     |     |     |    |
| CAC | TCT | GCG | CTG | AGG | CCT | GTC | CCT | GGC | CAG | GGC | CTG | AGT | CTC | AGC | ATC | 240 |
| His | Ser | Ala | Leu | Arg | Pro | Val | Pro | Gly | Gln | Gly | Leu | Ser | Leu | Ser | Ile |    |
| 65  |     |     |     |     | 70  |     |     |     |     | 75  |     |     |     |     | 80  |    |
| TCC | GAC | TCC | TCC | ATC | CGG | GTC | CAG | GGC | AGG | TGG | AAG | GTG | CGC | AAG | TCA | 288 |
| Ser | Asp | Ser | Ser | Ile | Arg | Val | Gln | Gly | Arg | Trp | Lys | Val | Arg | Lys | Ser |    |
|     |     |     |     | 85  |     |     |     |     | 90  |     |     |     |     | 95  |     |    |
| TTC | TTC | AAA | CTA | CAG | GGC | TCC | TTT | GAT | GTC | AGT | GTC | AAG | GGC | ATC | AGC | 336 |
| Phe | Phe | Lys | Leu | Gln | Gly | Ser | Phe | Asp | Val | Ser | Val | Lys | Gly | Ile | Ser |    |
|     |     |     |     | 100 |     |     |     |     | 105 |     |     |     |     | 110 |     |    |
| ATT | TCG | GTC | AAC | CTC | CTG | TTG | GGC | AGC | GAG | TCC | TCC | GGG | AGG | CCC | ACA | 384 |
| Ile | Ser | Val | Asn | Leu | Leu | Leu | Gly | Ser | Glu | Ser | Ser | Gly | Arg | Pro | Thr |    |
|     |     | 115 |     |     |     |     | 120 |     |     |     |     | 125 |     |     |     |    |
| GTT | ACT | GCC | TCC | AGC | TGC | AGC | AGT | GAC | ATC | GCT | GAC | GTG | GAG | GTG | GAC | 432 |

| Val | Thr | Ala | Ser | Ser | Cys | Ser | Ser | Asp | Ile | Ala | Asp | Val | Glu | Val | Asp |
| | 130 | | | | | 135 | | | | 140 | | | | | |

| ATG | TCG | GGA | GAC | TTG | GGG | TGG | CTG | TTG | AAC | CTC | TTC | CAC | AAC | CAG | ATT | 480 |
| Met | Ser | Gly | Asp | Leu | Gly | Trp | Leu | Leu | Asn | Leu | Phe | His | Asn | Gln | Ile | |
| 145 | | | | | 150 | | | | | 155 | | | | | 160 | |

| GAG | TCC | AAG | TTC | CAG | AAA | GTA | CTG | GAG | AGC | AGG | ATT | TGC | GAA | ATG | ATC | 528 |
| Glu | Ser | Lys | Phe | Gln | Lys | Val | Leu | Glu | Ser | Arg | Ile | Cys | Glu | Met | Ile | |
| | | | | 165 | | | | 170 | | | | | | 175 | | |

| CAG | AAA | TCG | GTG | TCC | TCC | GAT | CTA | CAG | CCT | TAT | CTC | CAA | ACT | CTG | CCA | 576 |
| Gln | Lys | Ser | Val | Ser | Ser | Asp | Leu | Gln | Pro | Tyr | Leu | Gln | Thr | Leu | Pro | |
| | | | 180 | | | | | 185 | | | | | | 190 | | |

| GTT | ACA | ACA | GAG | ATT | | | | | | | | | | | | 591 |
| Val | Thr | Thr | Glu | Ile | | | | | | | | | | | | |
| | | 195 | | | | | | | | | | | | | | |

( 2 ) INFORMATION FOR SEQ ID NO:4:

( i ) SEQUENCE CHARACTERISTICS:
        ( A ) LENGTH: 197 amino acids
        ( B ) TYPE: amino acid
        ( D ) TOPOLOGY: linear ( i i ) MOLECULE TYPE: protein ( i x ) FEATURE:
        ( A ) NAME/KEY: misc_feature
        ( D ) OTHER INFORMATION: "rLBP25"

( x i ) SEQUENCE DESCRIPTION: SEQ ID NO:4:

| Ala | Asn | Pro | Gly | Leu | Val | Ala | Arg | Ile | Thr | Asp | Lys | Gly | Leu | Gln | Tyr |
| 1 | | | | 5 | | | | | 10 | | | | | 15 | |

| Ala | Ala | Gln | Glu | Gly | Leu | Leu | Ala | Leu | Gln | Ser | Glu | Leu | Leu | Arg | Ile |
| | | | | 20 | | | | | 25 | | | | | 30 | |

| Thr | Leu | Pro | Asp | Phe | Thr | Gly | Asp | Leu | Arg | Ile | Pro | His | Val | Gly | Arg |
| | | | 35 | | | | | 40 | | | | | 45 | | |

| Gly | Arg | Tyr | Glu | Phe | His | Ser | Leu | Asn | Ile | His | Ser | Cys | Glu | Leu | Leu |
| | | 50 | | | | | 55 | | | | | 60 | | | |

| His | Ser | Ala | Leu | Arg | Pro | Val | Pro | Gly | Gln | Gly | Leu | Ser | Leu | Ser | Ile |
| 65 | | | | | 70 | | | | | 75 | | | | | 80 |

| Ser | Asp | Ser | Ser | Ile | Arg | Val | Gln | Gly | Arg | Trp | Lys | Val | Arg | Lys | Ser |
| | | | | 85 | | | | | 90 | | | | | 95 | |

| Phe | Phe | Lys | Leu | Gln | Gly | Ser | Phe | Asp | Val | Ser | Val | Lys | Gly | Ile | Ser |
| | | | 100 | | | | | 105 | | | | | 110 | | |

| Ile | Ser | Val | Asn | Leu | Leu | Leu | Gly | Ser | Glu | Ser | Ser | Gly | Arg | Pro | Thr |
| | | 115 | | | | | 120 | | | | | 125 | | | |

| Val | Thr | Ala | Ser | Ser | Cys | Ser | Ser | Asp | Ile | Ala | Asp | Val | Glu | Val | Asp |
| | 130 | | | | | 135 | | | | 140 | | | | | |

| Met | Ser | Gly | Asp | Leu | Gly | Trp | Leu | Leu | Asn | Leu | Phe | His | Asn | Gln | Ile |
| 145 | | | | | 150 | | | | | 155 | | | | | 160 |

| Glu | Ser | Lys | Phe | Gln | Lys | Val | Leu | Glu | Ser | Arg | Ile | Cys | Glu | Met | Ile |
| | | | | 165 | | | | | 170 | | | | | 175 | |

| Gln | Lys | Ser | Val | Ser | Ser | Asp | Leu | Gln | Pro | Tyr | Leu | Gln | Thr | Leu | Pro |
| | | | 180 | | | | | 185 | | | | | 190 | | |

| Val | Thr | Thr | Glu | Ile |
| | | 195 | | |

( 2 ) INFORMATION FOR SEQ ID NO:5:

( i ) SEQUENCE CHARACTERISTICS:
        ( A ) LENGTH: 1443 base pairs
        ( B ) TYPE: nucleic acid ( C ) STRANDEDNESS: single
( D ) TOPOLOGY: linear ( i i ) MOLECULE TYPE: DNA ( i x ) FEATURE:
    ( A ) NAME/KEY: CDS
    ( B ) LOCATION: 1..1443

( i x ) FEATURE:
    ( A ) NAME/KEY: mat_peptide
    ( B ) LOCATION: 76..1443

( i x ) FEATURE:
    ( A ) NAME/KEY: misc_feature
    ( D ) OTHER INFORMATION: "rLBP"

( x i ) SEQUENCE DESCRIPTION: SEQ ID NO:5:

```
ATG  GGG  GCC  TTG  GCC  AGA  GCC  CTG  CCG  TCC  ATA  CTG  CTG  GCA  TTG  CTG           48
Met  Gly  Ala  Leu  Ala  Arg  Ala  Leu  Pro  Ser  Ile  Leu  Leu  Ala  Leu  Leu
-25            -20                      -15                      -10

CTT  ACG  TCC  ACC  CCA  GAG  GCT  CTG  GGT  GCC  AAC  CCC  GGC  TTG  GTC  GCC           96
Leu  Thr  Ser  Thr  Pro  Glu  Ala  Leu  Gly  Ala  Asn  Pro  Gly  Leu  Val  Ala
                    -5                       1                       5

AGG  ATC  ACC  GAC  AAG  GGA  CTG  CAG  TAT  GCG  GCC  CAG  GAG  GGG  CTA  TTG          144
Arg  Ile  Thr  Asp  Lys  Gly  Leu  Gln  Tyr  Ala  Ala  Gln  Glu  Gly  Leu  Leu
          10                      15                      20

GCT  CTG  CAG  AGT  GAG  CTG  CTC  AGG  ATC  ACG  CTG  CCT  GAC  TTC  ACC  GGG          192
Ala  Leu  Gln  Ser  Glu  Leu  Leu  Arg  Ile  Thr  Leu  Pro  Asp  Phe  Thr  Gly
          25                      30                      35

GAC  TTG  AGG  ATC  CCC  CAC  GTC  GGC  CGT  GGG  CGC  TAT  GAG  TTC  CAC  AGC          240
Asp  Leu  Arg  Ile  Pro  His  Val  Gly  Arg  Gly  Arg  Tyr  Glu  Phe  His  Ser
40                       45                      50                       55

CTG  AAC  ATC  CAC  AGC  TGT  GAG  CTG  CTT  CAC  TCT  GCG  CTG  AGG  CCT  GTC          288
Leu  Asn  Ile  His  Ser  Cys  Glu  Leu  Leu  His  Ser  Ala  Leu  Arg  Pro  Val
                    60                       65                      70

CCT  GGC  CAG  GGC  CTG  AGT  CTC  AGC  ATC  TCC  GAC  TCC  TCC  ATC  CGG  GTC          336
Pro  Gly  Gln  Gly  Leu  Ser  Leu  Ser  Ile  Ser  Asp  Ser  Ser  Ile  Arg  Val
               75                       80                      85

CAG  GGC  AGG  TGG  AAG  GTG  CGC  AAG  TCA  TTC  TTC  AAA  CTA  CAG  GGC  TCC          384
Gln  Gly  Arg  Trp  Lys  Val  Arg  Lys  Ser  Phe  Phe  Lys  Leu  Gln  Gly  Ser
          90                       95                      100

TTT  GAT  GTC  AGT  GTC  AAG  GGC  ATC  AGC  ATT  TCG  GTC  AAC  CTC  CTG  TTG          432
Phe  Asp  Val  Ser  Val  Lys  Gly  Ile  Ser  Ile  Ser  Val  Asn  Leu  Leu  Leu
     105                      110                      115

GGC  AGC  GAG  TCC  TCC  GGG  AGG  CCC  ACA  GTT  ACT  GCC  TCC  AGC  TGC  AGC          480
Gly  Ser  Glu  Ser  Ser  Gly  Arg  Pro  Thr  Val  Thr  Ala  Ser  Ser  Cys  Ser
120                      125                      130                      135

AGT  GAC  ATC  GCT  GAC  GTG  GAG  GTG  GAC  ATG  TCG  GGA  GAC  TTG  GGG  TGG          528
Ser  Asp  Ile  Ala  Asp  Val  Glu  Val  Asp  Met  Ser  Gly  Asp  Leu  Gly  Trp
                    140                      145                      150

CTG  TTG  AAC  CTC  TTC  CAC  AAC  CAG  ATT  GAG  TCC  AAG  TTC  CAG  AAA  GTA          576
Leu  Leu  Asn  Leu  Phe  His  Asn  Gln  Ile  Glu  Ser  Lys  Phe  Gln  Lys  Val
               155                      160                      165

CTG  GAG  AGC  AGG  ATT  TGC  GAA  ATG  ATC  CAG  AAA  TCG  GTG  TCC  TCC  GAT          624
Leu  Glu  Ser  Arg  Ile  Cys  Glu  Met  Ile  Gln  Lys  Ser  Val  Ser  Ser  Asp
          170                      175                      180

CTA  CAG  CCT  TAT  CTC  CAA  ACT  CTG  CCA  GTT  ACA  ACA  GAG  ATT  GAC  AGT          672
Leu  Gln  Pro  Tyr  Leu  Gln  Thr  Leu  Pro  Val  Thr  Thr  Glu  Ile  Asp  Ser
     185                      190                      195

TTC  GCC  GAC  ATT  GAT  TAT  AGC  TTA  GTG  GAA  GCC  CCT  CGG  GCA  ACA  GCC          720
Phe  Ala  Asp  Ile  Asp  Tyr  Ser  Leu  Val  Glu  Ala  Pro  Arg  Ala  Thr  Ala
200                      205                      210                      215

CAG  ATG  CTG  GAG  GTG  ATG  TTT  AAG  GGT  GAA  ATC  TTT  CAT  CGT  AAC  CAC          768
```

|     |     |     |     |     |     |     |     |     |     |     |     |     |     |     |     |     |
|---|---|---|---|---|---|---|---|---|---|---|---|---|---|---|---|---|
| | Gln | Met | Leu | Glu | Val<br>220 | Met | Phe | Lys | Gly | Glu<br>225 | Ile | Phe | His | Arg | Asn<br>230 | His |
| CGT<br>Arg | TCT<br>Ser | CCA<br>Pro | GTT<br>Val<br>235 | ACC<br>Thr | CTC<br>Leu | CTT<br>Leu | GCT<br>Ala | GCA<br>Ala<br>240 | GTC<br>Val | ATG<br>Met | AGC<br>Ser | CTT<br>Leu | CCT<br>Pro<br>245 | GAG<br>Glu | GAA<br>Glu | 816 |
| CAC<br>His | AAC<br>Asn | AAA<br>Lys<br>250 | ATG<br>Met | GTC<br>Val | TAC<br>Tyr | TTT<br>Phe | GCC<br>Ala<br>255 | ATC<br>Ile | TCG<br>Ser | GAT<br>Asp | TAT<br>Tyr | GTC<br>Val<br>260 | TTC<br>Phe | AAC<br>Asn | ACG<br>Thr | 864 |
| GCC<br>Ala | AGC<br>Ser<br>265 | CTG<br>Leu | GTT<br>Val | TAT<br>Tyr | CAT<br>His | GAG<br>Glu<br>270 | GAA<br>Glu | GGA<br>Gly | TAT<br>Tyr | CTG<br>Leu | AAC<br>Asn<br>275 | TTC<br>Phe | TCC<br>Ser | ATC<br>Ile | ACA<br>Thr | 912 |
| GAT<br>Asp<br>280 | GAG<br>Glu | ATG<br>Met | ATA<br>Ile | CCG<br>Pro | CCT<br>Pro<br>285 | GAC<br>Asp | TCT<br>Ser | AAT<br>Asn | ATC<br>Ile | CGA<br>Arg<br>290 | CTG<br>Leu | ACC<br>Thr | ACC<br>Thr | AAG<br>Lys | TCC<br>Ser<br>295 | 960 |
| TTC<br>Phe | CGA<br>Arg | CCC<br>Pro | TTC<br>Phe | GTC<br>Val<br>300 | CCA<br>Pro | CGG<br>Arg | TTA<br>Leu | GCC<br>Ala | AGG<br>Arg<br>305 | CTC<br>Leu | TAC<br>Tyr | CCC<br>Pro | AAC<br>Asn | ATG<br>Met<br>310 | AAC<br>Asn | 1008 |
| CTG<br>Leu | GAA<br>Glu | CTC<br>Leu | CAG<br>Gln<br>315 | GGA<br>Gly | TCA<br>Ser | GTG<br>Val | CCC<br>Pro | TCT<br>Ser<br>320 | GCT<br>Ala | CCG<br>Pro | CTC<br>Leu | CTG<br>Leu | AAC<br>Asn<br>325 | TTC<br>Phe | AGC<br>Ser | 1056 |
| CCT<br>Pro | GGG<br>Gly | AAT<br>Asn<br>330 | CTG<br>Leu | TCT<br>Ser | GTG<br>Val | GAC<br>Asp | CCC<br>Pro<br>335 | TAT<br>Tyr | ATG<br>Met | GAG<br>Glu | ATA<br>Ile | GAT<br>Asp<br>340 | GCC<br>Ala | TTT<br>Phe | GTG<br>Val | 1104 |
| CTC<br>Leu | CTG<br>Leu<br>345 | CCC<br>Pro | AGC<br>Ser | TCC<br>Ser | AGC<br>Ser | AAG<br>Lys<br>350 | GAG<br>Glu | CCT<br>Pro | GTC<br>Val | TTC<br>Phe | CGG<br>Arg<br>355 | CTC<br>Leu | AGT<br>Ser | GTG<br>Val | GCC<br>Ala | 1152 |
| ACT<br>Thr<br>360 | AAT<br>Asn | GTG<br>Val | TCC<br>Ser | GCC<br>Ala | ACC<br>Thr<br>365 | TTG<br>Leu | ACC<br>Thr | TTC<br>Phe | AAT<br>Asn | ACC<br>Thr<br>370 | AGC<br>Ser | AAG<br>Lys | ATC<br>Ile | ACT<br>Thr | GGG<br>Gly<br>375 | 1200 |
| TTC<br>Phe | CTG<br>Leu | AAG<br>Lys | CCA<br>Pro | GGA<br>Gly<br>380 | AAG<br>Lys | GTA<br>Val | AAA<br>Lys | GTG<br>Val | GAA<br>Glu<br>385 | CTG<br>Leu | AAA<br>Lys | GAA<br>Glu | TCC<br>Ser | AAA<br>Lys<br>390 | GTT<br>Val | 1248 |
| GGA<br>Gly | CTA<br>Leu | TTC<br>Phe | AAT<br>Asn<br>395 | GCA<br>Ala | GAG<br>Glu | CTG<br>Leu | TTG<br>Leu | GAA<br>Glu<br>400 | GCG<br>Ala | CTC<br>Leu | CTC<br>Leu | AAC<br>Asn | TAT<br>Tyr<br>405 | TAC<br>Tyr | ATC<br>Ile | 1296 |
| CTT<br>Leu | AAC<br>Asn | ACC<br>Thr<br>410 | TTC<br>Phe | TAC<br>Tyr | CCC<br>Pro | AAG<br>Lys | TTC<br>Phe<br>415 | AAT<br>Asn | GAT<br>Asp | AAG<br>Lys | TTG<br>Leu | GCC<br>Ala<br>420 | GAA<br>Glu | GGC<br>Gly | TTC<br>Phe | 1344 |
| CCC<br>Pro | CTT<br>Leu<br>425 | CCT<br>Pro | CTG<br>Leu | CTG<br>Leu | AAG<br>Lys | CGT<br>Arg<br>430 | GTT<br>Val | CAG<br>Gln | CTC<br>Leu | TAC<br>Tyr | GAC<br>Asp<br>435 | CTT<br>Leu | GGG<br>Gly | CTG<br>Leu | CAG<br>Gln | 1392 |
| ATC<br>Ile<br>440 | CAT<br>His | AAG<br>Lys | GAC<br>Asp | TTC<br>Phe | CTG<br>Leu<br>445 | TTC<br>Phe | TTG<br>Leu | GGT<br>Gly | GCC<br>Ala | AAT<br>Asn<br>450 | GTC<br>Val | CAA<br>Gln | TAC<br>Tyr | ATG<br>Met | AGA<br>Arg<br>455 | 1440 |
| GTT<br>Val | | | | | | | | | | | | | | | | 1443 |

( 2 ) INFORMATION FOR SEQ ID NO:6:

( i ) SEQUENCE CHARACTERISTICS:
        ( A ) LENGTH: 481 amino acids
        ( B ) TYPE: amino acid
        ( D ) TOPOLOGY: linear ( i i ) MOLECULE TYPE: protein ( i x ) FEATURE:
        ( A ) NAME/KEY: misc_feature
        ( D ) OTHER INFORMATION: "rLBP"

( x i ) SEQUENCE DESCRIPTION: SEQ ID NO:6:

| Met | Gly | Ala | Leu | Ala | Arg | Ala | Leu | Pro | Ser | Ile | Leu | Leu | Ala | Leu | Leu |
|---|---|---|---|---|---|---|---|---|---|---|---|---|---|---|---|
| -25 | | | | -20 | | | | | -15 | | | | | -10 | |

| | | | | | | | | | | | | | | |
|---|---|---|---|---|---|---|---|---|---|---|---|---|---|---|
| Leu | Thr | Ser | Thr | Pro -5 | Glu | Ala | Leu | Gly | Ala 1 | Asn | Pro | Gly | Leu 5 | Val | Ala |
| Arg | Ile | Thr 10 | Asp | Lys | Gly | Leu | Gln 15 | Tyr | Ala | Ala | Gln | Gly 20 | Leu | Leu |
| Ala | Leu 25 | Gln | Ser | Glu | Leu | Leu 30 | Arg | Ile | Thr | Leu | Pro 35 | Asp | Phe | Thr | Gly |
| Asp 40 | Leu | Arg | Ile | Pro | His 45 | Val | Gly | Arg | Gly | Arg 50 | Tyr | Glu | Phe | His | Ser 55 |
| Leu | Asn | Ile | His | Ser 60 | Cys | Glu | Leu | Leu | His 65 | Ser | Ala | Leu | Arg | Pro 70 | Val |
| Pro | Gly | Gln | Gly 75 | Leu | Ser | Leu | Ser | Ile 80 | Ser | Asp | Ser | Ser | Ile 85 | Arg | Val |
| Gln | Gly | Arg 90 | Trp | Lys | Val | Arg | Lys 95 | Ser | Phe | Phe | Lys | Leu 100 | Gln | Gly | Ser |
| Phe | Asp 105 | Val | Ser | Val | Lys | Gly 110 | Ile | Ser | Ile | Ser | Val 115 | Asn | Leu | Leu | Leu |
| Gly 120 | Ser | Glu | Ser | Ser | Gly 125 | Arg | Pro | Thr | Val | Thr 130 | Ala | Ser | Ser | Cys | Ser 135 |
| Ser | Asp | Ile | Ala | Asp 140 | Val | Glu | Val | Asp | Met 145 | Ser | Gly | Asp | Leu | Gly 150 | Trp |
| Leu | Leu | Asn | Leu 155 | Phe | His | Asn | Gln | Ile 160 | Glu | Ser | Lys | Phe | Gln 165 | Lys | Val |
| Leu | Glu | Ser 170 | Arg | Ile | Cys | Glu | Met 175 | Ile | Gln | Lys | Ser | Val 180 | Ser | Ser | Asp |
| Leu | Gln 185 | Pro | Tyr | Leu | Gln | Thr 190 | Leu | Pro | Val | Thr | Thr 195 | Glu | Ile | Asp | Ser |
| Phe 200 | Ala | Asp | Ile | Asp | Tyr 205 | Ser | Leu | Val | Glu | Ala 210 | Pro | Arg | Ala | Thr | Ala 215 |
| Gln | Met | Leu | Glu | Val 220 | Met | Phe | Lys | Gly | Glu 225 | Ile | Phe | His | Arg | Asn 230 | His |
| Arg | Ser | Pro | Val 235 | Thr | Leu | Leu | Ala | Ala 240 | Val | Met | Ser | Leu | Pro 245 | Glu | Glu |
| His | Asn | Lys 250 | Met | Val | Tyr | Phe | Ala 255 | Ile | Ser | Asp | Tyr | Val 260 | Phe | Asn | Thr |
| Ala | Ser 265 | Leu | Val | Tyr | His | Glu 270 | Glu | Gly | Tyr | Leu | Asn 275 | Phe | Ser | Ile | Thr |
| Asp 280 | Glu | Met | Ile | Pro | Pro 285 | Asp | Ser | Asn | Ile | Arg 290 | Leu | Thr | Thr | Lys | Ser 295 |
| Phe | Arg | Pro | Phe | Val 300 | Pro | Arg | Leu | Ala | Arg 305 | Leu | Tyr | Pro | Asn | Met 310 | Asn |
| Leu | Glu | Leu | Gln 315 | Gly | Ser | Val | Pro | Ser 320 | Ala | Pro | Leu | Leu | Asn 325 | Phe | Ser |
| Pro | Gly | Asn 330 | Leu | Ser | Val | Asp | Pro 335 | Tyr | Met | Glu | Ile | Asp 340 | Ala | Phe | Val |
| Leu | Leu 345 | Pro | Ser | Ser | Ser | Lys 350 | Glu | Pro | Val | Phe | Arg 355 | Leu | Ser | Val | Ala |
| Thr 360 | Asn | Val | Ser | Ala | Thr 365 | Leu | Thr | Phe | Asn | Thr 370 | Ser | Lys | Ile | Thr | Gly 375 |
| Phe | Leu | Lys | Pro | Gly 380 | Lys | Val | Lys | Val | Glu 385 | Leu | Lys | Glu | Ser | Lys 390 | Val |
| Gly | Leu | Phe | Asn 395 | Ala | Glu | Leu | Leu | Glu 400 | Ala | Leu | Leu | Asn | Tyr 405 | Tyr | Ile |
| Leu | Asn | Thr | Phe | Tyr | Pro | Lys | Phe | Asn | Asp | Lys | Leu | Ala | Glu | Gly | Phe |

|  | | 410 | | | | 415 | | | | | 420 | | |
|---|---|---|---|---|---|---|---|---|---|---|---|---|---|

Pro  Leu  Pro  Leu  Leu  Lys  Arg  Val  Gln  Leu  Tyr  Asp  Leu  Gly  Leu  Gln
425                          430                     435

Ile  His  Lys  Asp  Phe  Leu  Phe  Leu  Gly  Ala  Asn  Val  Gln  Tyr  Met  Arg
440                          445                     450                          455

Val ( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: misc_feature
        ( D ) OTHER INFORMATION: "LBP-10"

( x i ) SEQUENCE DESCRIPTION: SEQ ID NO:7:

GAGATCGATA GTTTCGCCGA C                                                                                          21

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: misc_feature
        ( D ) OTHER INFORMATION: "LBP-8"

( x i ) SEQUENCE DESCRIPTION: SEQ ID NO:8:

CTGGCTAACC GTGGGACG                                                                                              18

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: misc_feature
        ( D ) OTHER INFORMATION: "LBP-11"

( x i ) SEQUENCE DESCRIPTION: SEQ ID NO:9:

ACTATCGATC TCTGTTGTAA                                                                                            20

( 2 ) INFORMATION FOR SEQ ID NO:10:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: misc_feature ( D ) OTHER INFORMATION: "LBP- Bsm"

( x i ) SEQUENCE DESCRIPTION: SEQ ID NO:10:

GAATGCAGCC AACCCCGGCT TGGTCGCCA                                              29

( 2 ) INFORMATION FOR SEQ ID NO:11:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( i i ) MOLECULE TYPE: DNA ( i x ) FEATURE:
           ( A ) NAME/KEY: misc_feature
           ( D ) OTHER INFORMATION: "BPI-63"

( x i ) SEQUENCE DESCRIPTION: SEQ ID NO:11:

AAAATCGATT CTGTGGCTGG                                                         20

( 2 ) INFORMATION FOR SEQ ID NO:12:

( i ) SEQUENCE CHARACTERISTICS:
           ( A ) LENGTH: 18 base pairs
           ( B ) TYPE: nucleic acid
           ( C ) STRANDEDNESS: single
           ( D ) TOPOLOGY: linear ( i i ) MOLECULE TYPE: DNA ( i x ) FEATURE:
           ( A ) NAME/KEY: misc_feature
           ( D ) OTHER INFORMATION: "BPI-7"

( x i ) SEQUENCE DESCRIPTION: SEQ ID NO:12:

GAACTTGGTT GTCAGTCG                                                           18

( 2 ) INFORMATION FOR SEQ ID NO:13:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( i i ) MOLECULE TYPE: DNA ( i x ) FEATURE:
           ( A ) NAME/KEY: misc_feature
           ( D ) OTHER INFORMATION: "BPI-64"

( x i ) SEQUENCE DESCRIPTION: SEQ ID NO:13:

AGAATCGATT TTGGTCATTA                                                         20

( 2 ) INFORMATION FOR SEQ ID NO:14:

( i ) SEQUENCE CHARACTERISTICS:
           ( A ) LENGTH: 18 base pairs
           ( B ) TYPE: nucleic acid
           ( C ) STRANDEDNESS: single
           ( D ) TOPOLOGY: linear ( i i ) MOLECULE TYPE: DNA

```
     ( i x ) FEATURE:
            ( A ) NAME/KEY: misc_feature
            ( D ) OTHER INFORMATION: "BPI-40"

( x i ) SEQUENCE DESCRIPTION: SEQ ID NO:14:

TGATCTGAAG CTGGGCAG                                                                    1 8
```

METHOD FOR POTENTIATING BPI PROTEIN PRODUCT BACTERICIDAL ACTIVITY BY ADMINISTRATION OF LBP PROTEIN PRODUCTS

This is a continuation-in-part of U.S. patent application Ser. No. 08/093,201 filed Jul. 14, 1993, now abandoned.

BACKGROUND OF THE INVENTION

The present invention relates generally to methods of treating gram-negative bacterial infections and the sequelae thereof and more specifically to the use of bactericidal/permeability-increasing protein (BPI) and BPI protein products in treatment of such infections.

BPI is a protein isolated from the granules of mammalian polymorphonuclear leukocytes (PMNs), which are blood cells essential in the defense against invading microorganisms. Human BPI protein has been isolated from polymorphonuclear neutrophils by acid extraction combined with either ion exchange chromatography [Elsbach, *J. Biol. Chem.*, 254:11000 (1979)] or *E. coli* affinity chromatography [Weiss et al., *Blood*, 69:652 (1987)] referred to herein as natural BPI and has potent bactericidal activity against a broad spectrum of gram-negative bacteria. The molecular weight of human BPI is approximately 55,000 daltons (55 kD). The amino acid sequence of the entire human BPI protein, as well as the DNA encoding the protein, have been elucidated in FIG. 1 of Gray et al., *J. Biol. Chem.*, 264:9505 (1989), incorporated herein by reference.

The bactericidal effect of BPI has been shown to be highly specific to sensitive gram-negative species, while being non-toxic for other microorganisms and for eukaryotic cells. The precise mechanism by which BPI kills bacteria is as yet unknown, but it is known that BPI must first attach to the surface of susceptible gram-negative bacteria. This initial binding of BPI to the bacteria involves electrostatic and hydrophobic interactions between the basic BPI protein and the negatively charged sites on lipopolysaccharides (LPS). LPS has been referred to as "endotoxin" because of the potent inflammatory response that it stimulates. LPS induces the release of mediators by host inflammatory cells which may ultimately result in irreversible endotoxic shock. BPI binds to lipid A, the most toxic and most biologically active component of LPS.

In susceptible bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. Elsbach and Weiss, *Inflammation: Basic Principles and Clinical Correlates*, eds. Gallin et al., Chapter 30, Review Press, Ltd. (1992). BPI is thought to act in two stages. The first is a sublethal stage that is characterized by immediate growth arrest, permeabilization of the outer membrane and selective activation of bacterial enzymes that hydrolyze phospholipids and peptidoglycan. Bacteria at this stage can be rescued by plating on serum albumin supplemented media. The second stage, defined by growth inhibition that cannot be reversed by serum albumin, occurs after prolonged exposure of the bacteria to BPI and is characterized by extensive physiologic and structural changes, including penetration of the cytoplasmic membrane.

BPI is also capable of neutralizing the endotoxic properties of LPS to which it binds. Because of its gram negative bactericidal properties and its ability to neutralize LPS, BPI can be utilized for the treatment of mammals suffering from diseases caused by Gram-negative bacteria, such as bacteremia or sepsis.

A proteolytic fragment corresponding to the N-terminal portion of human BPI holoprotein possesses substantially all the antibacterial efficacy of the naturally-derived 55 kD human holoprotein. In contrast to the N-terminal portion, the C-terminal region of the isolated human BPI protein displays only slightly detectable anti-bacterial activity. Ooi et al., *J. Exp. Med.*, 174:649 (1991). A BPI N-terminal fragment, which is the expression product of a gene encoding the first 199 amino acid residues of the human BPI holoprotein and comprising approximately the first 193 to 199 amino acid residues of human BPI hgoloprotein and referred to as "rBPI$_{23}$", has been produced by recombinant means as a 23 kD protein. Gazzano-Santoro et al., *Infect. Immun.* 60:4754–4761 (1992).

Lipopolysaccharide binding protein (LBP) is a 60 kD glycoprotein synthesized in the liver which shows significant structural homology with BPI. LBP is found in the serum of normal humans at levels of 5–10 μg/mL but can reach levels of 50–100 μg/mL in septic patients. Schumann et al., *Science*, 249:1429 (1990) disclose the amino acid sequences and encoding cDNA of both human and rabbit LBP. Like BPI, LBP has a binding site for lipid A and binds to the LPS from rough (R-) and smooth (S-) form bacteria. Unlike BPI, LBP does not possess significant bactericidal activity. BPI has been observed to neutralize and inhibit LPS-induced TNF production resulting from interaction of LBP with CD14 on monocytes and macrophages. Marra et al., *J. Immunol.* 148: 532 (1992), Weiss et al., *J. Clin. Invest.* 90: 1122 (1992). In contrast, LBP is observed to enhance LPS-induced TNF production. Wright et al., *Science*, 249:1131 (1990). Thus, in contrast to BPI, LBP has been recognized as an immunostimulatory molecule. See, e.g., Seilhamer, PCT International Application WO 93/06228 which discloses a variant form of LBP which it terms LBP-β.

Recently, it has been discovered that there exist biologically active protein derivatives of LBP which are characterized by the ability to bind to LPS but which lack CD14-mediated immunostimulatory properties of the LBP holoprotein. Specifically, co-owned and copending U.S. patent application Ser. No. 08/261,660 (Gazzano-Santoro et al., "Lipopolysaccharide Binding Protein Derivatives") filed Jun. 17, 1994, which is a continuation-in-part of U.S. patent application Ser. No. 08/079,510 filed Jun. 17, 1993 the disclosures of which are hereby incorporated by reference, discloses LBP protein derivatives and LBP derivative hybrid proteins which are capable of binding LPS and which lack CD14-mediated immunostimulatory activity. Preferred LBP protein derivatives have been produced by recombinant expression of genes encoding amino terminal amino acid residues, such as amino acid residues 1–197, and the resulting protein designated rLBP$_{25}$.

Of interest to the present application are the disclosures of references which relate to the potentiation of BPI bactericidal activity by 15 kD proteins derived from the granules of rabbit PMNs designated p15. Ooi et al., *J. Biol. Chem.*, 265:15956 (1990) disclose two related 15 kD proteins derived from rabbit PMN granules which have no bactericidal activity by themselves but which potentiate the first sublethal stage of BPI antibacterial activity but have an inhibitory effect on the second lethal stage of BPI antibacterial activity. Levy et al., *J. Biol. Chem.*, 268: 6058–6063 (1993) disclose the sequences of cDNAs encoding the two rabbit proteins and report that the protein with the stronger potentiating effect reduces the required dose of BPI for the early bacteriostatic effect by about 20-fold.

SUMMARY OF THE INVENTION

The present invention provides methods and compositions for treating gram negative bacterial infections and the sequelae thereof in a subject comprising administering a BPI protein product in combination with an LBP protein product. The invention is based on the finding that LBP protein products potentiate the bactericidal properties of BPI protein products by as much as almost ten thousand fold. The potentiation is seen in both the early reversible stage of BPI activity as well as in the late, irreversible stage of BPI activity. The result is unexpected because no similar potentiating molecules have been described that act at both the early and late stages of BPI killing, because unlike BPI, LBP does not possess significant bactericidal activity, and because an excess of LBP over BPI (as exists physiologically in serum) might be expected to competitively inhibit the bactericidal activity of BPI by virtue of its binding with LPS on a bacterial cell surface. This result is further unexpected as the effects of LBP holoproteins are generally viewed as being of a harmful nature as the LBP holoprotein has an immunostimulatory effect leading to an undesirable cytokine cascade.

According to the invention, LBP protein products can be coadministered with BPI protein products in amounts effective to potentiate the bactericidal properties of the BPI protein product. The invention utilizes any of the large variety of BPI proteins and protein derivatives known to the art including BPI protein fragments and hybrid BPI protein molecules. While any of the variety of LBP protein products known to the art are contemplated to be useful according to the teachings of the invention, those LBP protein derivatives which lack CD14 mediated immunostimulatory properties and particularly those lacking the ability to mediate LPS activity through the CD14 receptor are preferred for use. Such LBP protein products would include $rBPI_{25}$, LBP derivative hybrid proteins including LBP/BPI hybrid proteins and LBP-Ig fusion proteins which are characterized by the ability to bind LPS but which lack CD-14 immunostimulatory activity. Also contemplated are dimeric forms of $rLBP_{25}$ such as those obtained by fusion with human gamma heavy chain hinge and Fc regions, similar Fc fusions which lack $CH_2$ and dimers formed by incorporation of reactive cysteines or other such moieties at the carboxy terminus of $LBP_{25}$. It is contemplated that such forms may have properties comparable or superior to endogenous LBP.

The combination of BPI protein product and LBP protein product may be administered systemically or topically to a subject suffering from a gram-negative bacterial infection. Topical administration can be in the form of salves, ophthalmic drops, or eardrops. The BPI protein product and LBP protein product can also be administered systemically, such as orally, intravenously, by intramuscular or subcutaneous injection, or aerosolized for pulmonary administration. In addition, the compositions of the invention can be used in a variety of in vitro uses such as use as a bactericide to decontaminate fluids and surfaces and to sterilize surgical and other medical equipment and implantable devices.

Numerous additional aspects and advantages of the invention will become apparent to those skilled in the art upon consideration of the following detailed description of the invention which describes presently preferred embodiments thereof.

DETAILED DESCRIPTION

Figure 1:
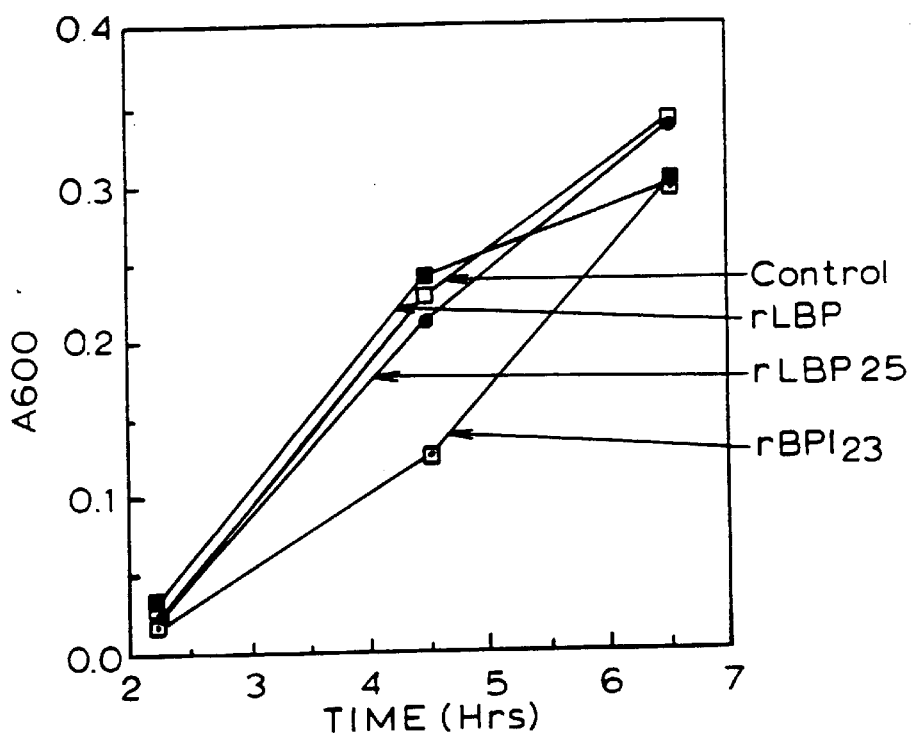
FIG. 1 depicts the results of a cell growth inhibition assay with rLBP, $rLBP_{25}$ and $rBPI_{23}$.

The present invention relates to methods of treating gram negative bacterial infections and the sequelae thereof in a subject comprising administering a BPI protein product and an LBP protein product. More specifically, the invention relates to the discovery that the co-administration of LBP protein products with BPI protein products potentiates activities including the gram-negative bactericidal activity of the BPI protein product. By "potentiate" is meant the ability to lower the effective concentration of BPI protein product that need be administered to achieve a particular effect such as a bactericidal effect. The LBP and BPI protein products may be coadministered or may be administered at various times one after another although it is generally preferred that the LBP protein product be administered prior to or simultaneously with the BPI protein product. The proteins may be administered systemically, such as intravenously, or by intramuscular or subcutaneous injection or may be administered topically. An advantage provided by the present invention is the ability to provide more effective systemic and topical treatment by virtue of the great potentiation of BPI anti-bacterial activity.

When practicing the methods of the invention, the LBP protein product is preferably an LBP protein derivative or LBP derivative hybrid protein which lacks CD14-mediated immunostimulatory properties according to co-owned and copending U.S. patent application Ser. No. 08/261,660 (Gazzano-Santoro et al., "Lipopolysaccharide Binding Protein Derivatives") filed Jun. 17, 1994, which is a continuation-in-part of U.S. patent application Ser. No. 08/079,510 filed Jun. 17, 1993 the disclosures of which are hereby incorporated by reference. Preferred LBP protein products which lack the CD-14-mediated immunostimulatory properties of the LBP holoprotein are amino-terminal LBP fragments such as those comprising the first 197 amino-terminal amino acids of the LBP holoprotein which is designated rLBP$_{25}$. Other suitable LBP protein products include LBP peptides which are able to bind to endotoxin and have the effect of potentiating bactericidal and other effects of BPI. Preferred LBP derivative hybrid proteins include LBP/BPI hybrid proteins and LBP-Ig fusion proteins which are characterized by the ability to bind LPS but which lack CD-14 immunostimulatory activity. Such LBP protein products are particularly preferred for use with the present invention because they do not exhibit the undesirable immunostimulatory properties of the LBP holoprotein.

The invention also provides improved methods of in vitro antisepsis for decontamination of fluids and surfaces comprising administering a BPI protein product in combination with an LBP protein product in an amount effective to potentiate the bactericidal properties of the BPI protein product. LBP protein products can be used to potentiate the bactericidal effects of BPI protein products in a variety of in vitro applications including sterilization of surgical and other medical equipment and implantable devices.

The invention further provides pharmaceutical compositions for treatment of gram-negative bacterial infection and the sequelae thereof comprising the combination of a BPI protein product and an LBP protein product which is present in an amount effective to potentiate the bactericidal properties of the BPI protein product. The pharmaceutical composition can comprise a pharmaceutically-acceptable diluent, adjuvant or carrier.

As another aspect of the invention, antiseptic bactericidal compositions are provided which comprise a BPI protein product and an LBP protein product in an amount effective to potentiate the bactericidal properties of the BPI protein product.

As used herein, "BPI protein product" includes naturally and recombinantly produced bactericidal/permeability-increasing protein; natural, synthetic, and recombinant biologically active polypeptide fragments of bactericidal/permeability increasing protein; and biologically active polypeptide analogs, including hybrid fusion proteins, of either bactericidal/permeability increasing protein or biologically active fragments thereof. The BPI protein products including biologically active fragments of BPI holoprotein which are to be administered according to the methods of this invention may be generated and/or isolated by any means known in the art. U.S. Pat. No. 5,198,541 the disclosure of which is hereby incorporated by reference discloses recombinant genes encoding and methods for expression of BPI proteins. Co-owned, copending U.S. patent application Ser. No. 07/885,501 filed May 19, 1992 and a continuation-in-part thereof, U.S. patent application Ser. No. 08/072,063 filed May 19, 1993 which are hereby incorporated by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI include biologically active molecules that contains the same amino acid sequence as a BPI holoprotein, except that the molecule lacks amino-terminal amino acids, internal amino acids, and/or carboxy-terminal amino acids of the holoprotein. By way of nonlimiting examples, such fragments include those described herein and a natural 25 kD fragment and a recombinant 23 kD amino-terminal fragment of the human BPI holoprotein referred to as rBPI$_{23}$. See, Gazzano-Santoro et al., Infect. Immun. 60:4754–4761 (1992). In that publication, an expression vector was used as a source of DNA encoding a recombinant expression product (rBPI$_{23}$) having the 31-residue signal sequence and encoding the first 199 amino acids of the N-terminus of the mature human BPI, as set out in SEQ ID NOS: 1 and 2 taken from Gray et al., supra, except that valine at position 151 is specified by GTG rather than GTC and residue 185 is glutamic acid (specified by GAG) rather than lysine (specified by AAG). Recombinant holoprotein having an approximate molecular weight of 50 kD and referred to herein as rBPI or as rBPI$_{50}$ has also been produced having the sequence set out in SEQ ID NOS: 1 and 2 taken from Gray et al., supra, with the exceptions noted for rBPI$_{23}$ and with the exception that residue 417 is alanine (specified by GCT) rather than valine (specified by GTT).

Biologically active analogs of BPI include but are not limited to recombinant hybrid fusion proteins comprising BPI holoprotein or biologically active fragment thereof, and at least a portion of at least one other polypeptide. Such proteins are described by Theofan et al. in co-owned, copending U.S. patent application Ser. No. 08/064,693 filed May 19, 1993, which is a continuation-in-part application of U.S. patent application Ser. No. 07/885,911, filed May 19, 1992, the disclosures of which are incorporated herein by reference in their entirety and include hybrid fusion proteins comprising, at the amino terminal end, a BPI protein or a biologically active fragment thereof and, at the carboxy terminal end, at least one constant domain of an immunoglobulin heavy chain or allelic variant thereof.

Biologically active analogs of BPI also include but are not limited to BPI protein products wherein one or more amino acid residue has been replaced by a different amino acid. For example, co-owned, copending U.S. patent application Ser. No. 08/013,801 (Theofan et al., "Stable Bactericidal/Permeability-Increasing Protein Products and Pharmaceutical Compositions Containing the Same," filed Feb. 2, 1993), which is incorporated herein by reference, discloses polypeptide analogs of BPI and BPI fragments wherein a cysteine residue at position 132 or at position 135 is replaced by a different amino acid. A preferred BPI protein product described by this application is the expression product of DNA encoding from amino acid 1 to approximately 193 or 199 of the N-terminal amino acids of BPI holoprotein, but wherein the cysteine at residue 132 is substituted with alanine and is designated $rBPI_{21}\Delta cys$ or $rBPI_{21}$. Alternative useful BPI protein products include those which are the expression products of DNA encoding from amino acid 1 to approximately 193 or 199 of the N-terminal amino acids of BPI halo protein but wherein the cysteine at residue 175 is substituted with alanine or wherein the serine at residue 18 is substituted with cysteine.

Other BPI protein products useful according to the methods of the invention are peptides based on or derived from BPI such as those described in co-owned and copending U.S. patent application Ser. No. 08/209,762 filed Mar. 11, 1994, which is a continuation-in-part U.S. patent application Ser. No. 08/183,222 filed Jan. 14, 1994, which is a continuation-in-part of U.S. patent application Ser. No. 08/093,202 filed Jul. 15, 1993 as continuation-in-part of U.S. patent application Ser. No. 08/030,644 filed Mar. 12, 1993. The disclosures of these applications are hereby incorporated by reference. Other useful BPI protein products include peptides based on or derived from BPI which are described in co-owned and copending U.S. patent application Ser. No. 08/274,299 filed Jul. 11, 1994 (abandoned) and U.S. patent application Ser. No. 08/273,540 filed Jul. 11, 1994 (abandoned), the disclosures of which are hereby incorporated by reference.

Still further BPI protein products useful according to the method of the invention include recombinant dimeric forms of a BPI protein product produced according to the methods disclosed in co-owned and copending U.S. patent application Ser. No. 08/212,132 filed Mar. 11, 1994 the disclosure of which is hereby incorporated by reference. Preferred dimeric products include dimeric BPI protein products wherein the monomers are amino terminal BPI fragments having amino acid residues of from about 1 to 175 to about I to 199 amino of the amino terminal of BPI holoprotein.

The invention further provides novel pharmaceutical compositions comprising combinations of BPI protein products and an LBP protein product in an amount effective to potentiate the bactericidal properties of the BPI protein product together with pharmaceutically acceptable diluents, adjuvants, and carriers. The compositions are useful in methods for treating a gram-negative bacterial infection, including the sequelae thereof such as endotoxin related hypotension and shock, and one or more of conditions associated therewith including fever, metabolic acidosis, disseminated intravascular coagulation and related clotting disorders, anemia, thrombocytopenia, leukopenia, adult respiratory distress syndrome and related pulmonary disorders, renal failure and related renal disorders, hepatobiliary disease and related central nervous system disorders. Such methods comprise administering an LBP protein derivative or LBP derivative hybrid protein to a subject suffering from a gram-negative bacterial infection, including the sequelae thereof.

When employed for treatment of a gram-negative bacterial infection, including the sequelae thereof, the BPI protein products and LBP protein products are preferably each administered parenterally and most preferably intravenously in amounts broadly ranging from about 0.1 milligram and about 100 milligrams per kilogram of body weight of the treated subject with preferred treatments ranging from about 1 milligrams and 25 milligrams per kilogram of body weight.

The administration of BPI protein products is preferably accomplished with a pharmaceutical composition comprising a BPI protein product and a pharmaceutically acceptable diluent, adjuvant, or carrier. The BPI protein product composition may be administered without or in conjunction with known antibiotics, surfactants, or other chemotherapeutic agents. Suitable antibiotics for use in combination with BPI protein products are disclosed in co-owned and copending U.S. patent application Ser. No. 08/273,401 filed Jul. 11, 1994 (abandoned), which is a continuation-in-part of U.S. patent application Ser. No. 08/125,651 filed on Sep. 22, 1993, the disclosures of which are incorporated herein by reference.

A preferred pharmaceutical composition containing BPI protein products comprises BPI at a concentration of 1 mg/ml in citrate buffered saline (0.02M citrate, 0.15M NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). A preferred pharmaceutical composition comprising 2 mg/mL $rBPI21\Delta cys$ contains 5 mM citrate, 150 mM NaCl, pH 5.0, 0.2% poloxamer 188 and 0.002% polysorbate 80. Such preferred combinations are described in co-owned, copending, U.S. patent application Ser. No. 08/251,576 giled May 31, 1994 which is a continuation-in-part of U.S. patent application Ser. No. 08/190,869 filed Feb. 2, 1994 which is a continuation in part of U.S patent application Ser. No. 08/012,360 (McGregor et al., "Improved Pharmaceutical Composition" filed Feb. 2, 1993), the disclosures of which are incorporated herein by reference.

As used herein, "LBP protein product" includes naturally and recombinantly produced lipopolysaccharide binding protein; natural, synthetic, and recombinant biologically active polypeptide fragments and derivatives of lipopolysaccharide binding protein; and biologically active polypeptide analogs, including hybrid fusion proteins, of either LBP or biologically active fragments thereof. LBP protein products useful according to the methods of the present invention include LBP holoprotein which can be produced by expression of recombinant genes in transformed eucaryotic host cells such as described in co-owned and copending U.S. patent application Ser. No. 08/261,660 (Gazzano-Santoro et al., "Lipopolysaccharide Binding Protein Derivatives" filed Jun. 17, 1994, which is a continuation-in-part of U.S. patent application Ser. No. 08/079,510 filed Jun. 17, 1993 the disclosures of which are hereby incorporated by reference and designated rLBP or $rLBP_{50}$. Also described in that application are LBP protein derivatives which lack CD14-mediated immunostimulatory properties and particularly the ability to mediate LPS activity through the CD14 receptor are preferred for use. Such LBP protein products are preferred for use according to the present invention because excessive CD14-mediated immunostimulation is generally considered undesirable, and is particularly so in subjects suffering from infection.

Preferred LBP protein derivatives are characterized as N-terminal fragments having a molecular weight of about 25 kD. Most preferred are LBP amino-terminal fragments characterized by the amino acid sequence of the first 197 amino acids of the amino-terminus of LBP, as set out in SEQ ID NOS:3 and 4 and designated rLBP$_{25}$. Nevertheless, it is contemplated that LBP protein derivatives considerably smaller than 25 kD and comprising substantially fewer than the first 197 amino acids of the amino-terminus of the holo-LBP molecule are suitable for use according to the invention provided they retain the ability to bind to LPS. Moreover, it is contemplated that LBP protein derivatives comprising greater than the first 197 amino acid residues of the holo-LBP molecule including amino acids on the carboxy-terminal side of first 197 amino acids of the rLBP as disclosed in SEQ ID NOS:5 and 6 will likewise prove useful according to the methods of the invention provided they lack an element that promotes CD14-mediated immunostimulatory activity. It is further contemplated that those of skill in the art are capable of making additions, deletions and substitutions of the amino acid residues of SEQ ID NOS:3–6 without loss of the desired biological activities of the molecules. Still further, LBP protein products may be obtained by deletion, substitution, addition or mutation, including mutation by site-directed mutagenesis of the DNA sequence encoding the LBP holoprotein, wherein the LBP protein product maintains LPS-binding activity and lacks CD14-mediated immunostimulatory activity. Specifically contemplated are LBP hybrid molecules and dimeric forms which may result in improved affinity of LBP for bacteria and/or increased stability in vivo. These include LBP/BPI hybrid proteins and LBP-Ig fusion proteins. Such hybrid proteins further include those using human gamma 1 or gamma 3 hinge regions to permit dimer formation. Other forms of dimer contemplated to have enhanced serum stability and binding affinity include fusions with Fc lacking the CH$_2$ domain, or hybrids using leucine or helix bundles.

The following detailed description relates to administration of BPI protein products in combination with LBP protein products in amounts effective to potentiate the bactericidal activity of the BPI protein products. More specifically, Example 1 relates to LBP potentiation of BPI bactericidal activity in a broth growth assay. Example 2 relates to LBP potentiation of BPI bactericidal activity in a plate assay. Example 3 relates to Actinomycin D permeability assays utilizing rBPI$_{23}$, rLBP and combinations thereof. Example 4 relates to cell growth inhibition assays relating to the effect of cell density on the potentiation effect. Example 5 relates to cell growth inhibition assays for rBPI$_{23}$, rLBP and combinations thereof in the presence of BSA. Example 6 relates to LBP potentiation of various BPI protein products in plate assays. Example 7 relates to LBP potentiation of BPI permeabilization activity with Actinomycin D. Example 8 relates to LBP potentiation of BPI activity in a bacterial protein synthesis assay. Example 9 relates to a plate growth bactericidal assay with rBPI$_{23}$ in combination with an LBP/BPI hybrid protein (LBP(1–197)/BPI(200– 456)). Example 10 relates to a plate growth bactericidal assay examining the effect of order of addition of rBPI$_{23}$ and rLBP on potentiation of BPI bactericidal activity.

EXAMPLE 1

LBP Protein Product Potentiation of BPI Bactericidal Activity in a Broth Assay

The effect of exemplary LBP protein products rLBP$_{25}$ and rLBP alone and in combination with an exemplary BPI protein product rBPI$_{23}$ on *E. coli* J5 grown to late log phase in a triethanolamine buffered minimal salt medium [TEA; Weiss et al., *J. Clin. Invest.* 65:619 (1980)] was determined. *E. coli* J5 is a rough UDP-galactose 4 epimerase negative mutant of the smooth strain 0111-B4. Specifically, the cells were grown overnight in TYE broth [Gazzano-Santoro et al., Infect. Immun. 60: 4754 (1992)] and then subcultured as a 1/200 dilution in TEA medium. The bacteria were harvested at late-logarithmic phase, washed and resuspended in 0.9% NaCl at an absorption calculated to obtain approximately $5\times10^8$ cells/mL. Ten $\mu$L of cells (~$5\times10^6$ cells) were incubated at 37° C. for 45 minutes in 200 $\mu$L of a buffered salts solution (10% Hanks Balanced Salts Solution, 40 mM Tris-HCl, pH 7.5, 0.10% casamino acids pH 7.4) with the BPI or LBP protein products. Two mL of nutrient broth was added and growth was followed for 6 hours.

The results of addition of either rLBP$_{25}$ or rLBP at 50 $\mu$g/mL to rBPI$_{23}$ at 1 $\mu$g/mL or a control (buffer) are illustrated in FIG. 1 and show that neither of the LBP protein products had a growth inhibitory effect in comparison to the BPI protein product.

Figure 2:
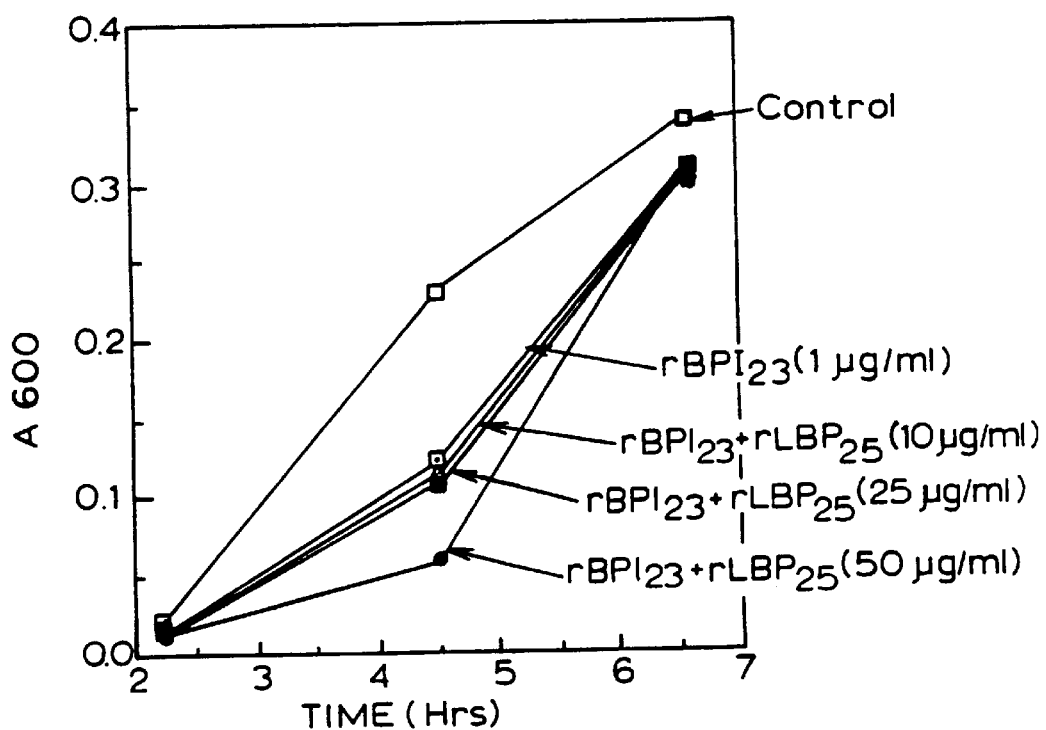
FIG. 2 depicts the results of a cell growth inhibition assay with $rBPI_{23}$ and combinations of $rBPI_{23}$ with various concentrations of $rLBP_{25}$.
Figure 3:
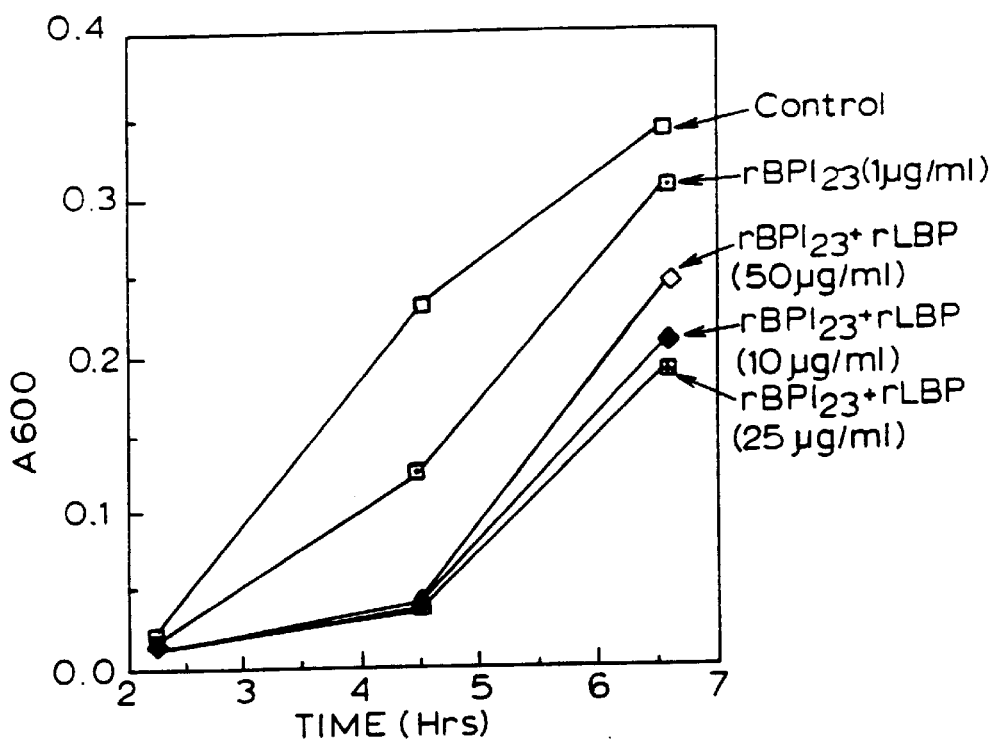
FIG. 3 depicts the results of a cell growth inhibition assay for $rBPI_{23}$ and combinations of rBPI23 with various concentrations of rLBP.

Next, the effect of an LBP protein product on the activity of a BPI protein product was measured. Specifically, rBPI$_{23}$ was administered at a concentration of 1 $\mu$g/mL in combination with either rLBP$_{25}$ or rLBP at concentrations of 10, 25 or 50 $\mu$g/mL. The results illustrated in FIGS. 2 and 3 show that rLBP$_{25}$ slightly enhances the bactericidal activity of rBPI$_{23}$ (FIG. 2) and that rLBP (holoprotein) significantly potentiates the bactericidal activity of rBPI$_{23}$ (FIG. 3).

The effect of rLBP at a concentration of 10 $\mu$g/mL was then determined at various BPI protein concentrations according to the general methods above but wherein growth was followed at A$_{600}$. According to a first experiment, rBPI$_{23}$ was administered at concentrations from 2 $\mu$g/mL to 0.1 $\mu$g/mL with and without rLBP at a concentration of 10 $\mu$g/mL. In the second experiment, rBPI$_{23}$ was administered at concentrations of from 0.5 $\mu$g/mL to 0.01 $\mu$g/mL with and without rLBP at a concentration of 10 $\mu$g/mL.

Figure 4:
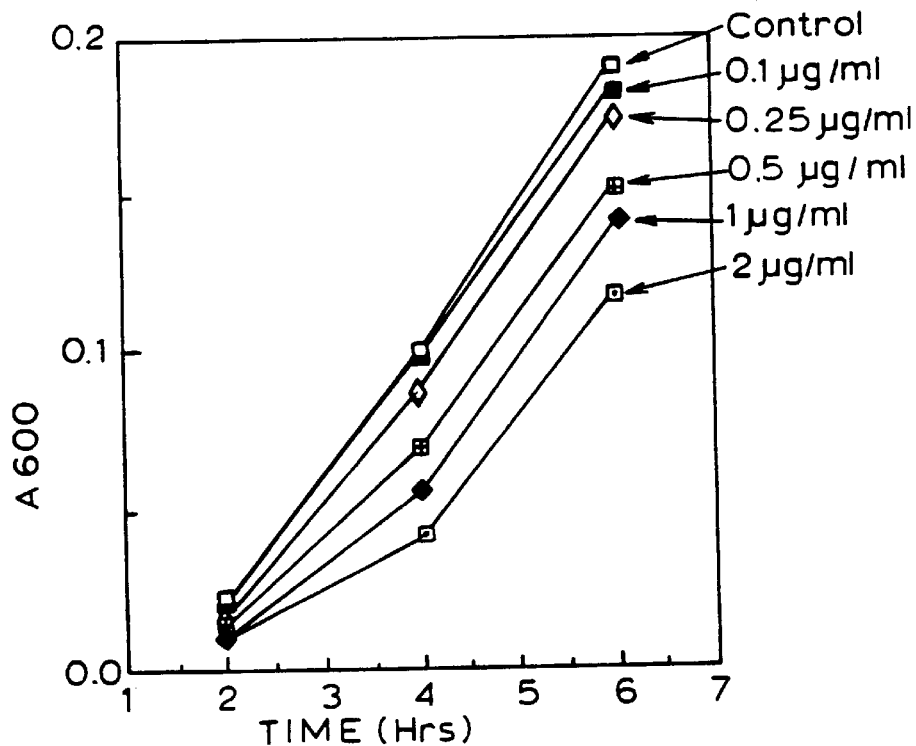
FIG. 4 depicts the results of a cell growth inhibition assay with $rBPI_{23}$ at various concentrations.
Figure 5:
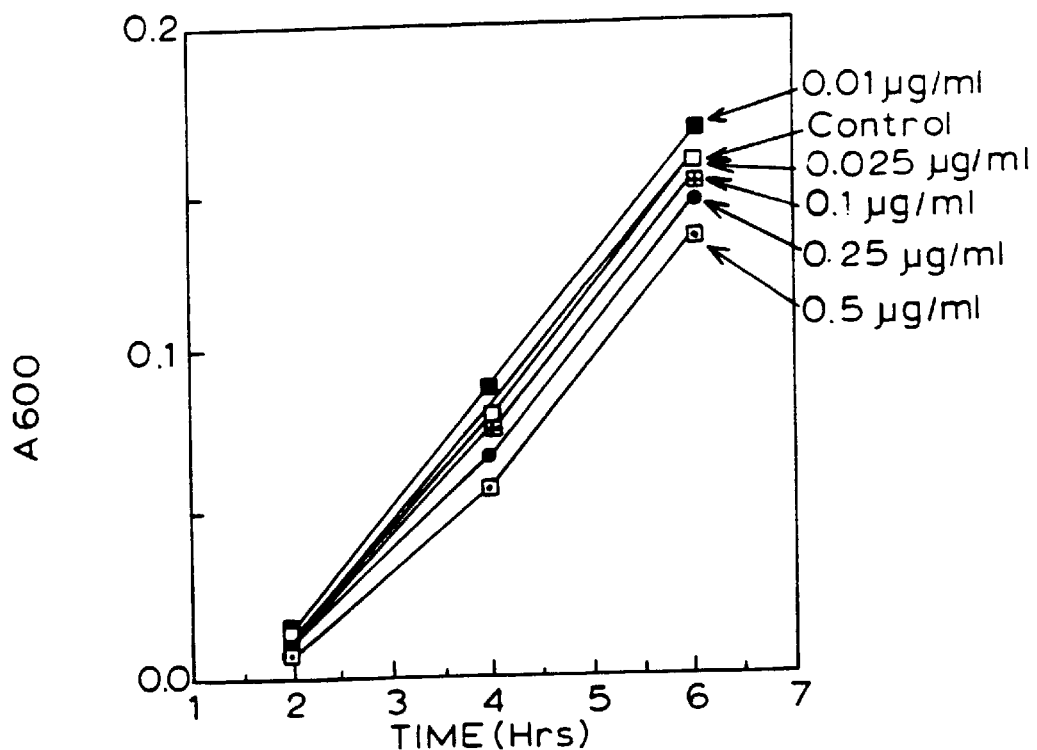
FIG. 5 depicts the results of a cell growth inhibition assay with $rBPI_{23}$ at various concentrations.
Figure 6:
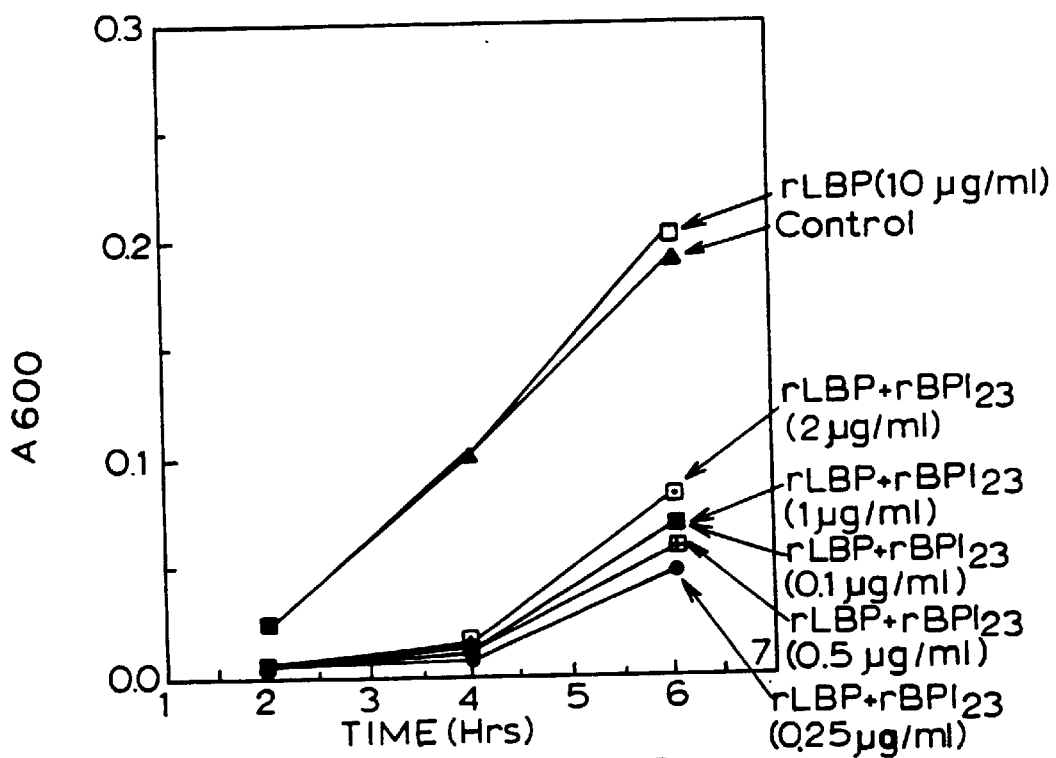
FIG. 6 depicts the results of a cell growth inhibition assay with rLBP and combinations of rLBP with various concentrations of $rBPI_{23}$.
Figure 7:
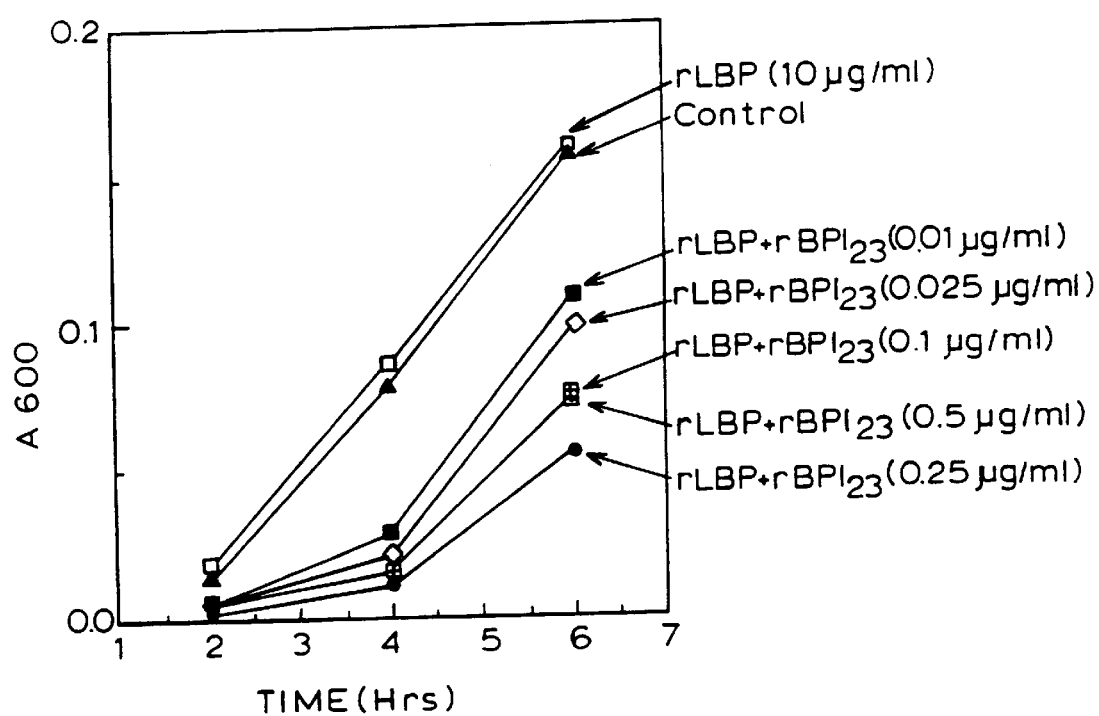
FIG. 7 depicts the results of a cell growth inhibition assay with LBP and combinations of rLBP and various concentrations of $rBPI_{23}$.

The results of administration of BPI protein alone illustrated in FIGS. 4 and 5 show that rBPI$_{23}$ alone has a measurable bactericidal effect only at concentrations at or above 0.5 $\mu$g/mL. The results illustrated in FIGS. 6 and 7 show a dramatic potentiation in the bactericidal activity of the BPI protein by coadministration of an LBP protein at 10 $\mu$g/mL. In both experiments, the maximal growth inhibitory effect was seen with administration of rLBP at 10 $\mu$g/mL with BPI$_{23}$ at a concentration of 0.25 $\mu$g/mL. The administration of rLBP alone had no inhibitory effect.

EXAMPLE 2

Potentiation as Determined in Plate Assays

The effect of exemplary LBP protein products on *E. coli* alone and in combination with an exemplary BPI protein product was studied in a plate growth assay to determine if the potentiation of BPI bactericidal activity by LBP results in a reduction of colony forming units. Specifically, *E. coli* J5 was grown to late log phase in TEA broth. Approximately $5\times10^6$ cells were incubated at 37° C. for 45 minutes in 200 $\mu$L of buffered salts solution (pH 7.4) with the rBPI$_{23}$ at concentrations of from 2.5 $\mu$g/mL to 0.001 $\mu$g/mL and/or with rLBP at 10 and 1 $\mu$g/mL. The samples were diluted in physiological saline and plated on nutrient agar.

Figure 8A:
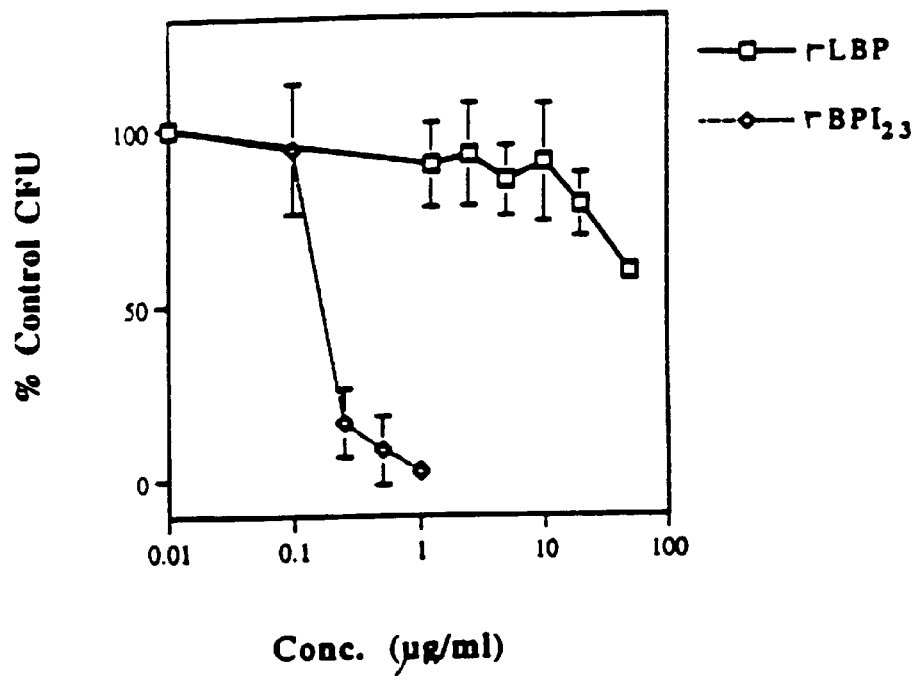
FIGS. 8a and 8b depict the results of a plate growth bactericidal assay with $rBPI_{23}$ and rLBP and combinations thereof.
Figure 8B:
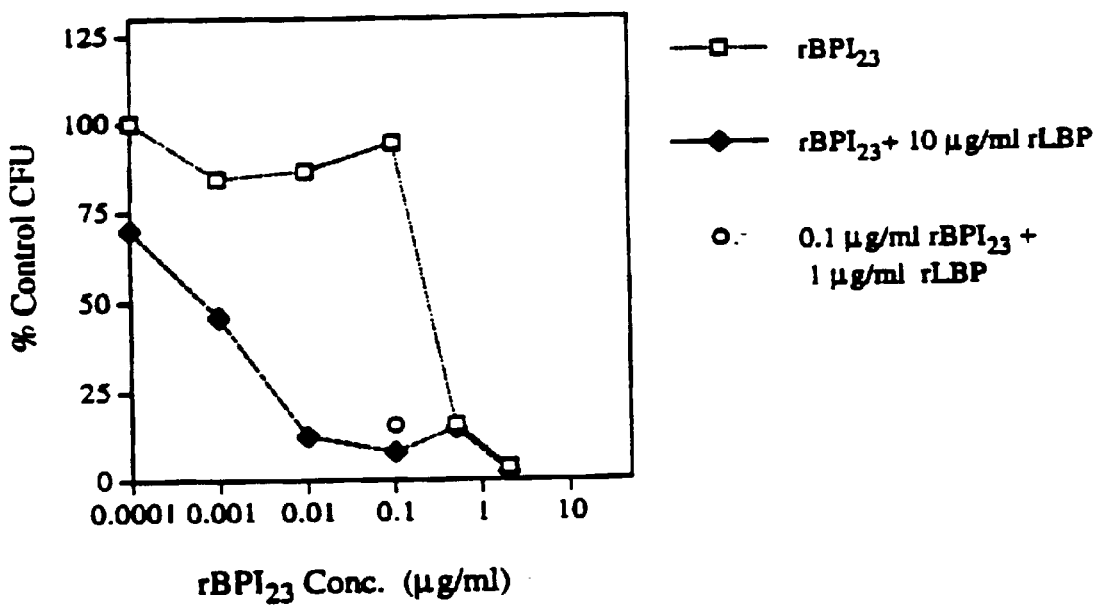

The results shown in FIG. 8a [wherein rBPI$_{23}$ is depicted by (—◇—) and rLBP is depicted by (—□—)] show that incubation of cells with rBPI$_{23}$ at about 1 $\mu$g/mL caused a 95% reduction in viable cell count but that incubation with rBPI$_{23}$ at or below 0.1 μg/mL failed to significantly reduce CFU relative to the negative control. Incubation with rLBP alone had no significant effect on the viable cell count at concentrations up to 10 μg/mL, but resulted in approximately 25% and 40% reductions in CFU at 20 and 50 μg/mL concentrations respectively. The results illustrated in FIG. 8b show that rLBP at 1 μg/mL (—○—) and 10 μg/mL (—◆—) potentiates the bactericidal activity of rBPI$_{23}$ compared to rBPI$_{23}$ alone (—□—).

Figure 9:
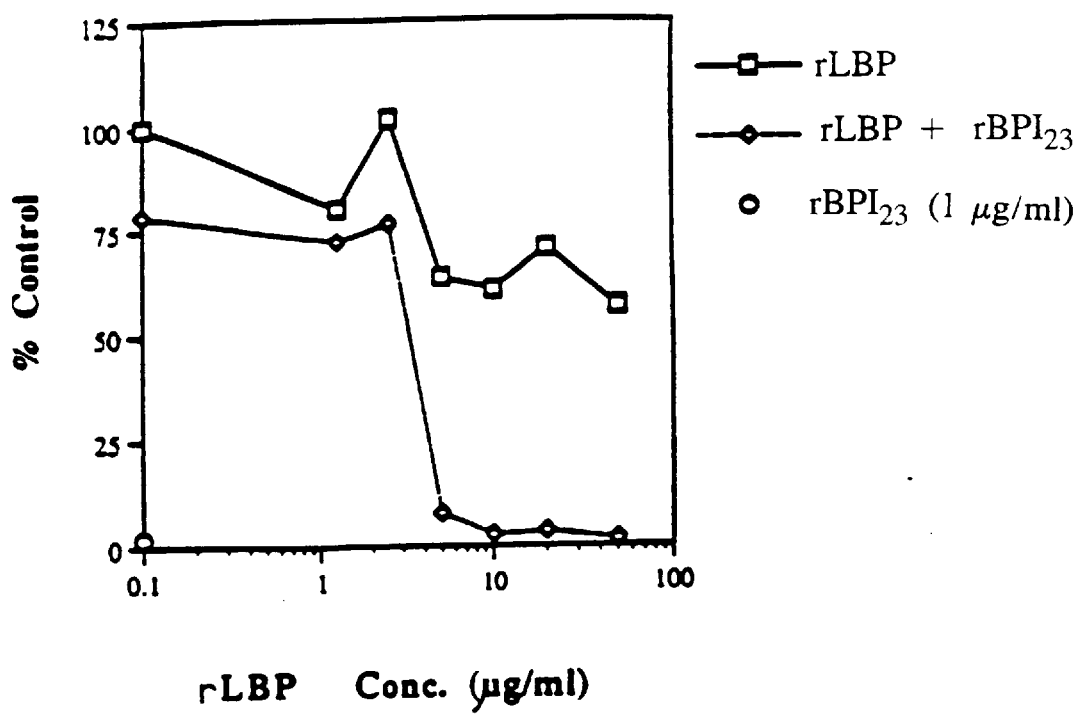
FIG. 9 depicts the results of a plate growth bactericidal assay with rLBP or $rBPI_{23}$ and the combination of rLBP with $rBPI_{23}$.
Figure 10:
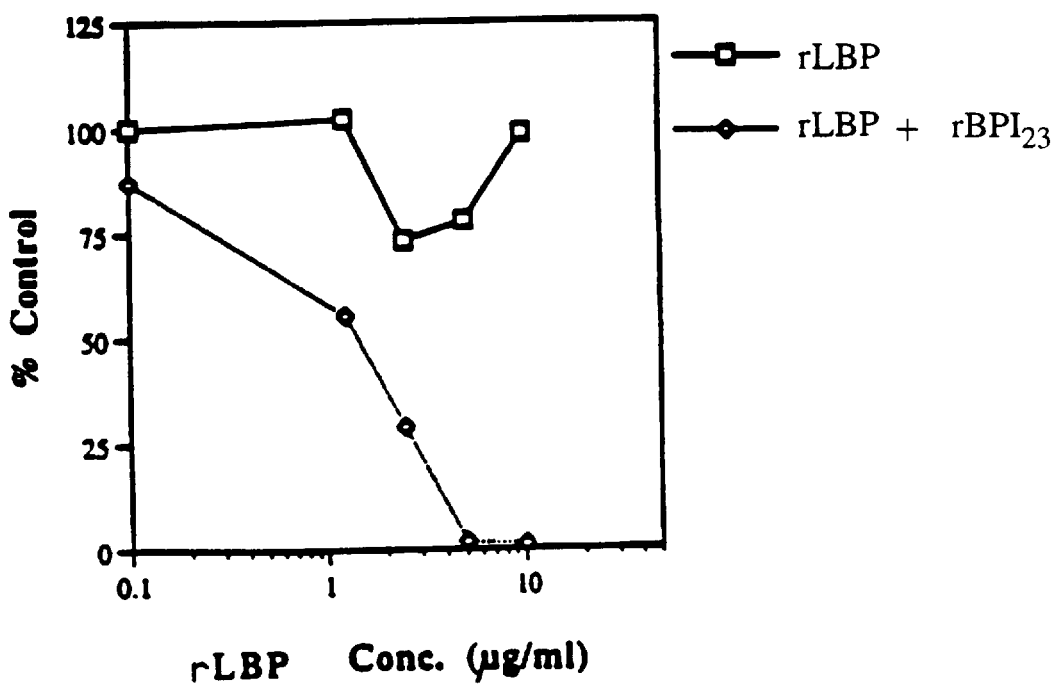
FIG. 10 depicts the results of a plate growth bactericidal assay with rLBP and the combination of rLBP with $rBPI_{23}$.
Figure 11:
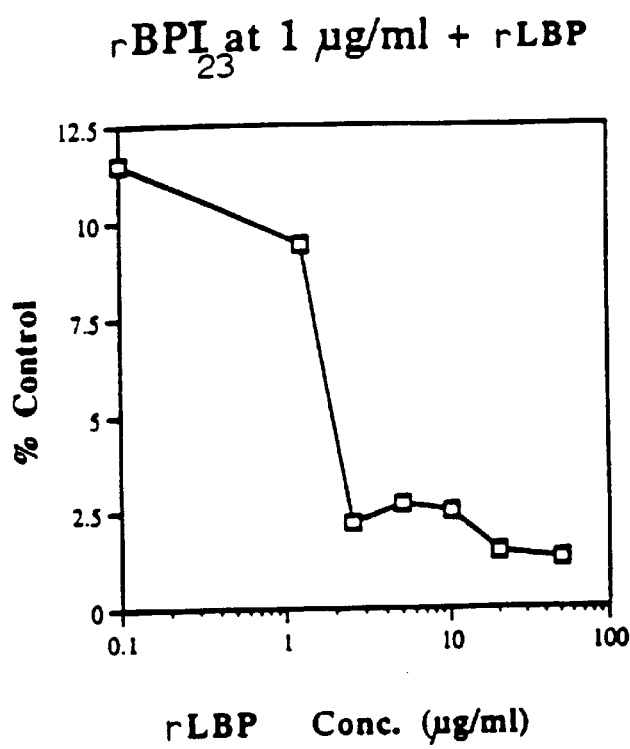
FIG. 11 depicts the results of a plate growth bactericidal assay with the combination of $rBPI_{23}$ with various concentrations of rLBP.

Additional plate assays were conducted to determine the effect of LBP protein product potentiation of BPI protein product bactericidal activity at various concentrations of both protein products. Specifically, approximately 4×10$^7$ cells/mL of E. coli J5 were incubated at 37° C. for about 45 minutes in 200 μL of buffered salts solution (pH 7.4) containing LBP at concentrations from 1 to 50 μg/mL and/or rBPI$_{23}$ at concentrations of 0.01, 0.1 and 1.0 μg/mL. The samples were diluted in physiological saline and plated on nutrient agar. The results of these experiments shown in FIGS. 9, 10 and 11 below indicate that rLBP alone has relatively little bactericidal activity but that it significantly enhances the bactericidal activity of rBPI$_{23}$, and particularly so at the lower BPI protein concentrations (0.1 and 0.01 μg/mL). In FIG. 9 rLBP the data is depicted as follows: rLBP, —□—; rLBP and rBPI$_{23}$ at 0.01 μg/mL, —◇— and rBPI$_{23}$ alone at 1 μg/mL —○—. In FIG. 10 the data are depicted as follows: rLBP, —□—; rLBP with rBPI$_{23}$ at 0.1 μg/mL, —◇—. In FIG. 11 the data are depicted as follows: rLBP with rBPI$_{23}$ at 1 μg/mL, —□—. These results indicated that the optimal effect was obtained with 5–10 μg/mL rLBP depending upon the concentration of rBPI$_{23}$.

Figure 12:
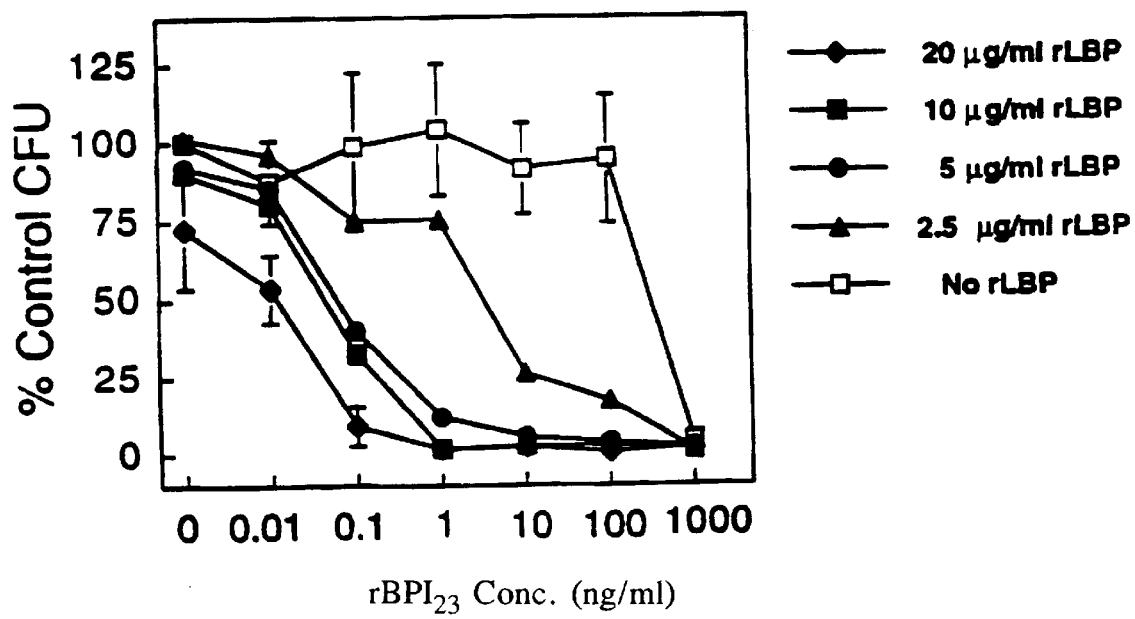
FIG. 12 depicts the results of a plate growth bactericidal assay with combinations of rLBP with $rBPI_{23}$ at various concentrations of $rBPI_{23}$ and rLBP.

Additional plate assays were conducted to further define the extent of LBP protein product potentiation of BPI protein products. Specifically, approximately 4×10$^7$ cells/mL of E. coli J5 were incubated at 37° C. for about 45 minutes in 200 μL of buffered salts solution (pH 7.4). The cells were then incubated with varying concentrations of rBPI$_{23}$ (1, 0.1, 0.01, 0.001, 0.0001 and 0.00001 μg/mL) and with various concentrations of rLBP (0, 1.25, 2.5, 5, 10, 20 and 50 μg/mL) for 45 minutes at 37° C., diluted in physiological saline and plated on nutrient agar. Selected results are shown in FIG. 12 with the data depicted as follows: rBPI$_{23}$ with no rLBP, —□—; rBPI$_{23}$ with 2.5 μg/mL rLBP, —▲—; rBPI$_{23}$ with 5 μg/mL rLBP, —●—; rBPI$_{23}$ with 10 μg/mL rLBP, —■—; and rBPI$_{23}$ with 20 μg/mL LBP, —◆—. The results suggest that the same extent of killing (~90–95%) is observed with 20 μg/mL rLBP with 0.1 ng/mL BPI$_{23}$ as with rBPI$_{23}$ at 1.0 μg/mL. This represents an approximate 10,000 fold potentiation of the bactericidal effects of BPI and suggests that a BPI/target cell ratio of only about 60 BPI molecules per cell is required to kill 90% of the cells.

Table 1 below shows the concentrations of rBPI$_{23}$ required to kill >95% of 4×10$^7$ E. coli J5 cells/mL in the presence of various concentrations of rLBP. The ratios were obtained by dividing the number of rLBP or rBPI$_{223}$ molecules per mL by 4×10$^7$. Only ~90% reduction in CFUs was achieved for the combination of 20 μg/mL rLBP with 0.1 ng/mL rBPI$_{23}$.

TABLE 1

| rLBP conc. (μg/mL) | rLBP conc. (Molecules/cell) | rBPI$_{23}$ conc. (ng/mL) | rBPI$_{23}$ conc. (Molecules/cell) |
|---|---|---|---|
| 0 | 0 | 1000 | ~600,000 |
| 5 | ~1,200,000 | 10 | ~6,000 |
| 10 | ~2,400,000 | 1 | ~600 |
| 20 | ~4,800,000 | 0.1 | ~60 |

Figure 13:
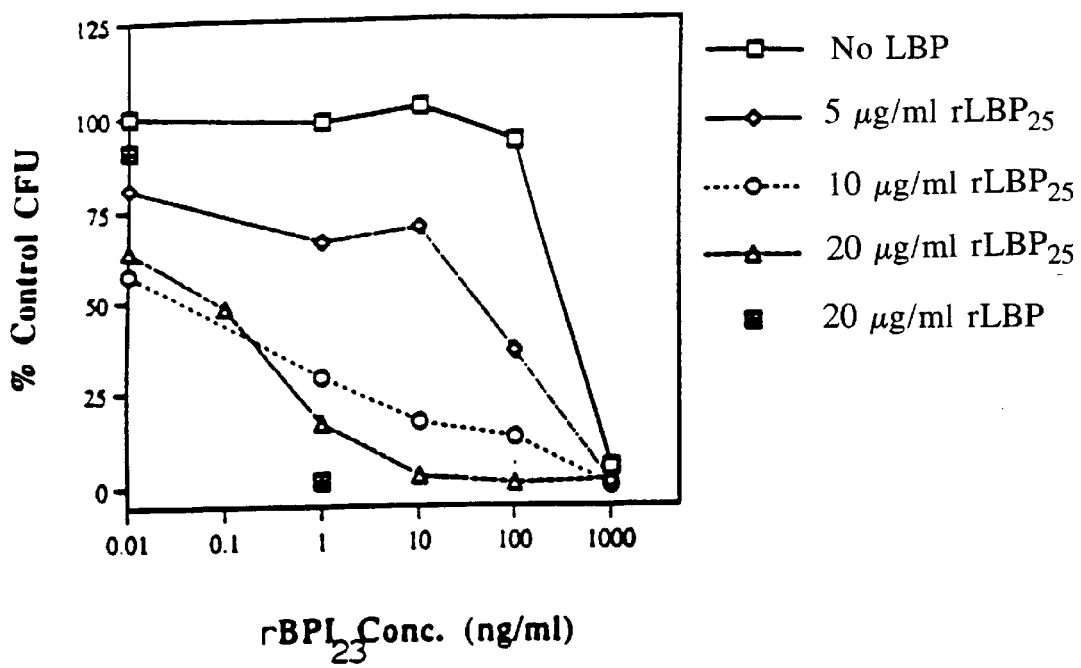
FIG. 13 depicts the results of a plate growth bactericidal assay with combinations of $rLBP_{25}$ with $rBPI_{23}$ at various concentrations of $rBPI_{23}$ and rLBP.

The experiment was then repeated substituting varying concentrations of rLBP$_{25}$ for rLBP with the results shown in FIG. 13. In that figure the data are depicted as follows: rBPI$_{23}$ with no rLBP, —□—; rBPI$_{23}$ with 5 μg/mL rLBP$_{25}$, —◇—; rBPI$_{23}$ with 10 μg/mL rLBP$_{25}$, —○—; rBPI$_{23}$ with 20 μg/mL rLBP$_{25}$, —△—; and rBPI$_{23}$ with 20 μg/mL LBP (a square containing a cross). The results shown in FIG. 13 indicate that rLBP$_{25}$ potentiates the bactericidal activity of rBPI$_{23}$ but that it is slightly less effective than rLBP at doing so.

Figure 14:
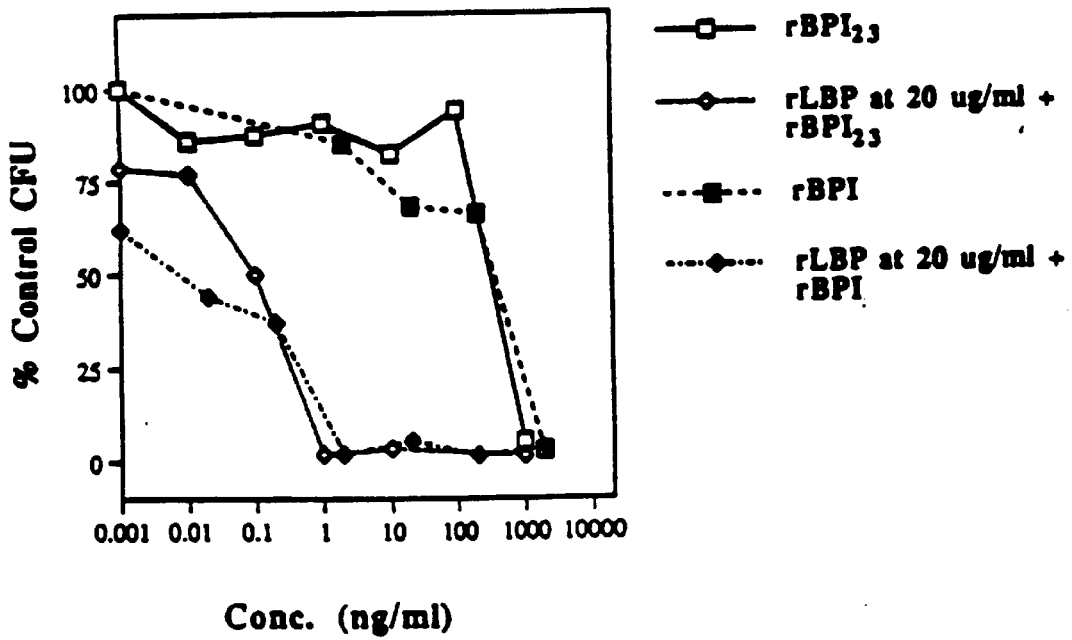
FIG. 14 depicts the results of a plate growth bactericidal assay with $rBPI_{23}$, rBPI and combinations of rLBP with various concentrations of $rBPI_{23}$ or rBPI.

The experiment was then further repeated utilizing rBPI with the results shown in FIG. 14. In that figure the data depicted as follows: rBPI$_{23}$ alone, —□—; rBPI$_{23}$ with 20 μg/mL rLBP, —◇—; rBPI alone (a square containing a cross) and rBPI with 20 μg/mL rBPI, —◆—. The results illustrated in FIG. 14 show that rLBP at 20 μg/mL also potentiated the activity of full-length recombinant BPI in a manner similar to that of rBPI$_{23}$.

EXAMPLE 3

Figure 15A:
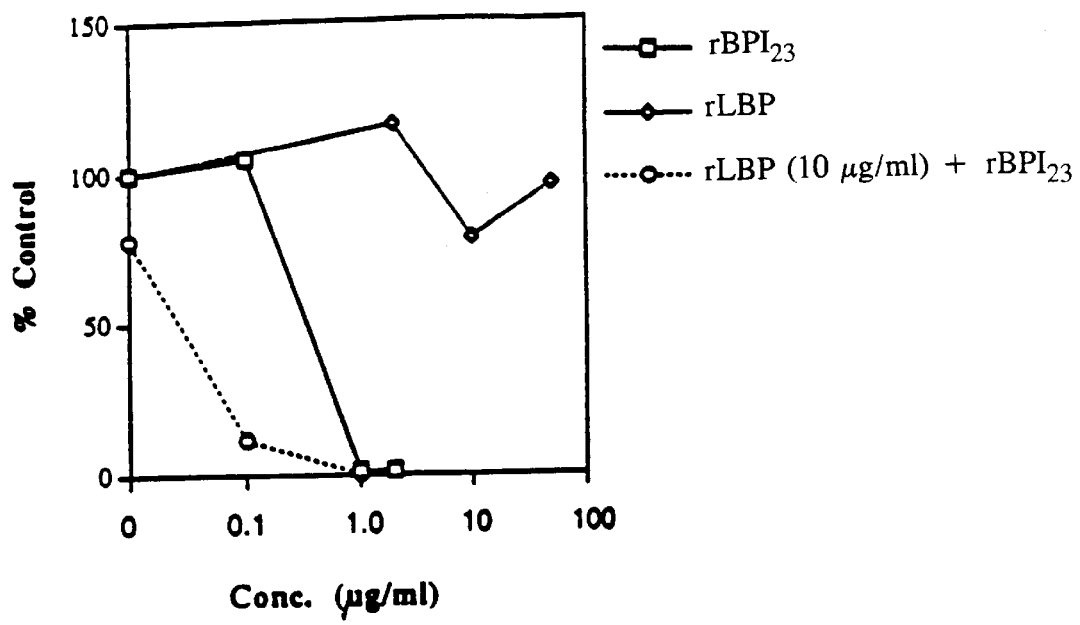
FIGS. 15a, 15b and 15c depict the results of Actinomycin D permeability assays utilizing $rBPI_{23}$, rLBP and combinations thereof.
Figure 15B:
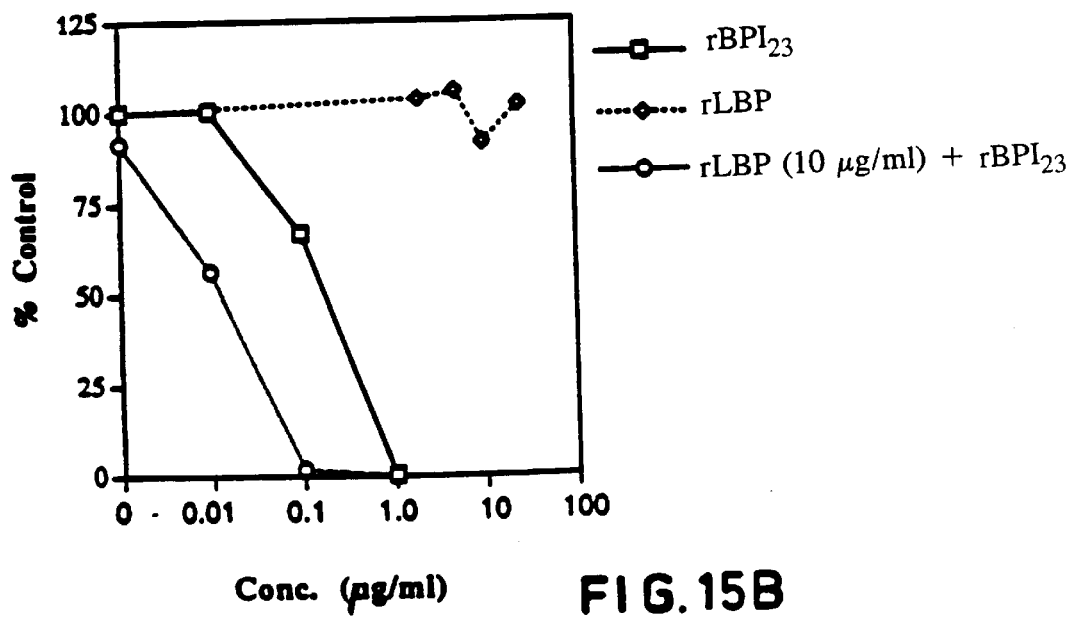
Figure 15C:
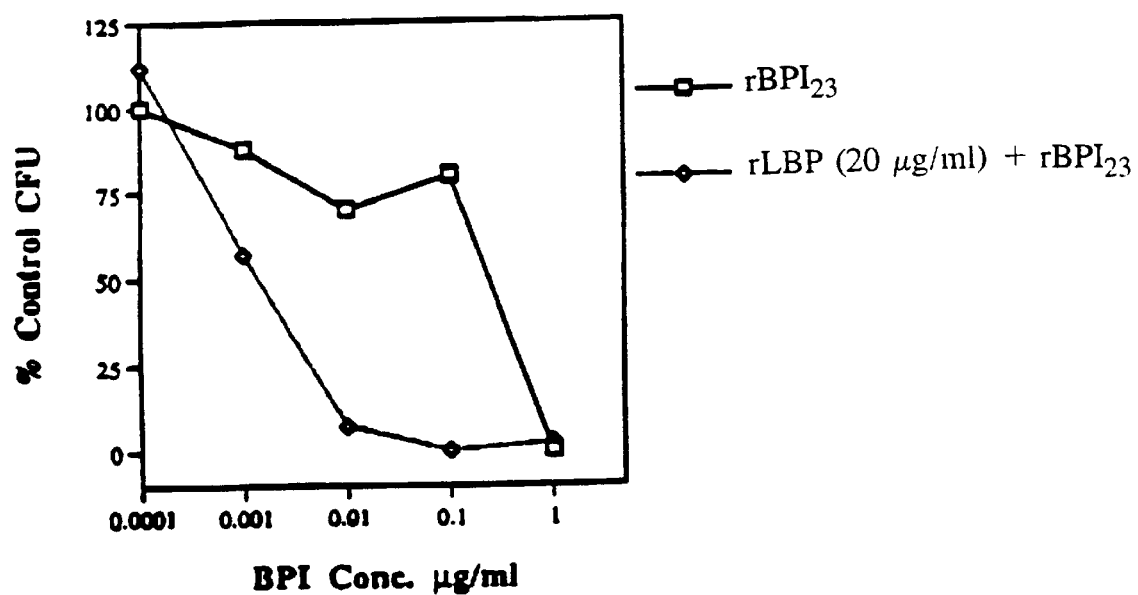

LBP Potentiation of BPI Permeabilization Activity with Actinomycin D in a Plate Assay The effect of LBP protein products on the permeability increasing properties of BPI protein products were determined in a plate assay. Specifically, approximately 4×10$^7$ cells/mL of E. coli J5 were incubated at 37° C. for 10 minutes in 200 μL of buffered salts solution (pH 7.4) containing actinomycin D at 50 g/mL and either rLBP at concentrations from 1 to 50 μg/mL or rBPI$_{23}$ at concentrations of from 0.01 to 2 μg/mL with or without rLBP at a concentration of 10 μg/mL and rBPI$_{23}$ at 0.001 to 1 μg/mL with rLBP at 20 μg/mL. The resulting samples were diluted in physiological saline and plated on nutrient agar supplemented with 0.1% BSA. The results of the two experiments which were performed with rLBP at 10 μg/mL and various concentrations of rBPI$_{23}$ are shown in FIGS. 15a and 15b. In FIGS. 15a and 15b the data are depicted as follows: rBPI$_{23}$ alone —□—; rLBP alone —◇—; and rBPI$_{23}$ in combination with rLBP at 10μg/mL, —○—. The results suggest that while rLBP has little or no permeabilizing activity by itself it is able to significantly enhance the permeabilizing activity of rBPI$_{23}$. Results of an experiment performed with rLBP at 20 μg/mL and rBPI$_{23}$ at various concentrations suggest that rLBP potentiates BPI at up to 100 fold as illustrated in FIG. 15c. In FIG. 15c. rBPI$_{23}$ alone is represented by (—□—), and rBPI$_{23}$ with 20 μg/mL rLBP is represented by (—◇—).

EXAMPLE 4

Figure 16:
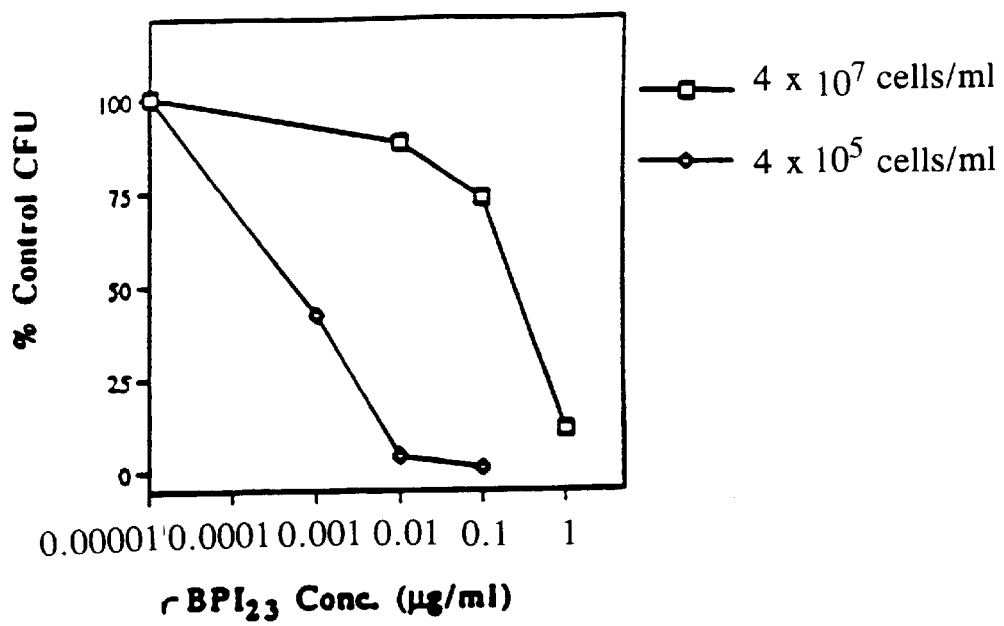
FIG. 16 depicts the results of a plate growth bactericidal assay with $rBPI_{23}$ using different cell densities.
Figure 17:
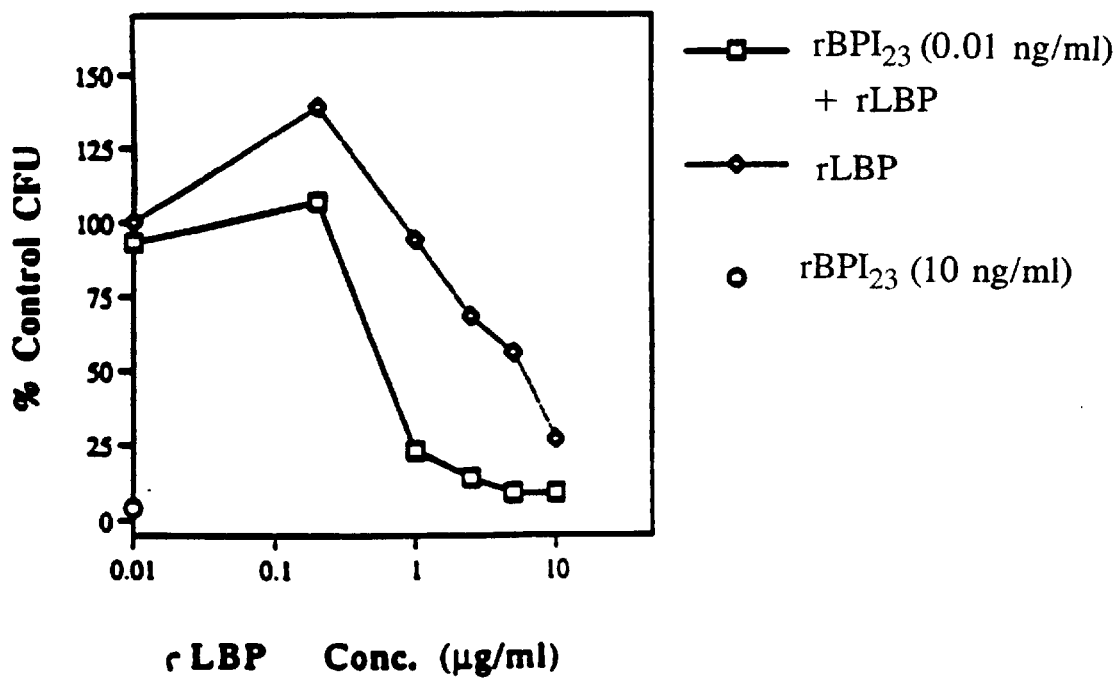
FIG. 17 depicts the results of a plate growth bactericidal assay with rLBP, $rBPI_{23}$ and combinations thereof using different cell densities.

Effects of Cell Density on LBP Potentiation of BPI Bactericidal Activity in a Plate Assay The effect of E. coli cell density on the potentiation effect was examined. Specifically, the concentration of rBPI required to kill approximately 90% of the cells (IC$_{90}$) was examined at $4\times10^7$ cells/mL versus $4\times10^5$ cells/mL and compared to the concentration of rBPI$_{23}$ needed to achieve the same degree of killing in the presence of rLBP at these cell densities. The results are shown in FIGS. 16 and 17. In FIG. 16 $4\times10^7$ cells/mL are represented by (—□—) and the $4\times10^5$ cells/mL are represented by (—◇—). In FIG. 17 the data are depicted as follows: rLBP with 0.01 ng/mL rBPI$_{23}$ —□—; rLBP alone —◇—; and rBPI$_{23}$ at 10 ng/mL, ○.

The results illustrated in FIGS. 16 and 17 show that when the *E. coli* concentration is reduced by 100-fold, i.e. from $4\times10^7$ cells/mL to 4×10G5G cells/mL, the concentration of BPI protein needed to achieve an IC$_{90}$ is also reduced by about 100-fold (i.e. from 1 μg/mL to 10 ng/mL rBPI$_{23}$ results in an IC$_{90}$). By comparison, at $4\times10^5$ cells/mL, an rLBP concentration of from 2.5 to 5 μg/mL in combination with 0.01 ng/mL of rBPI$_{23}$ (a concentration which is 1000-fold less than needed for rBPI$_{23}$ to achieve an IC$_{90}$ at this cell density) is needed to achieve an IC$_{90}$. Thus, at the lower cell density, the BPI killing effect is BPI/target ratio dependent while the LBP potentiation is more dependent on maintaining the concentration of LBP within a physiologically-relevant range.

EXAMPLE 5

Figure 18A:
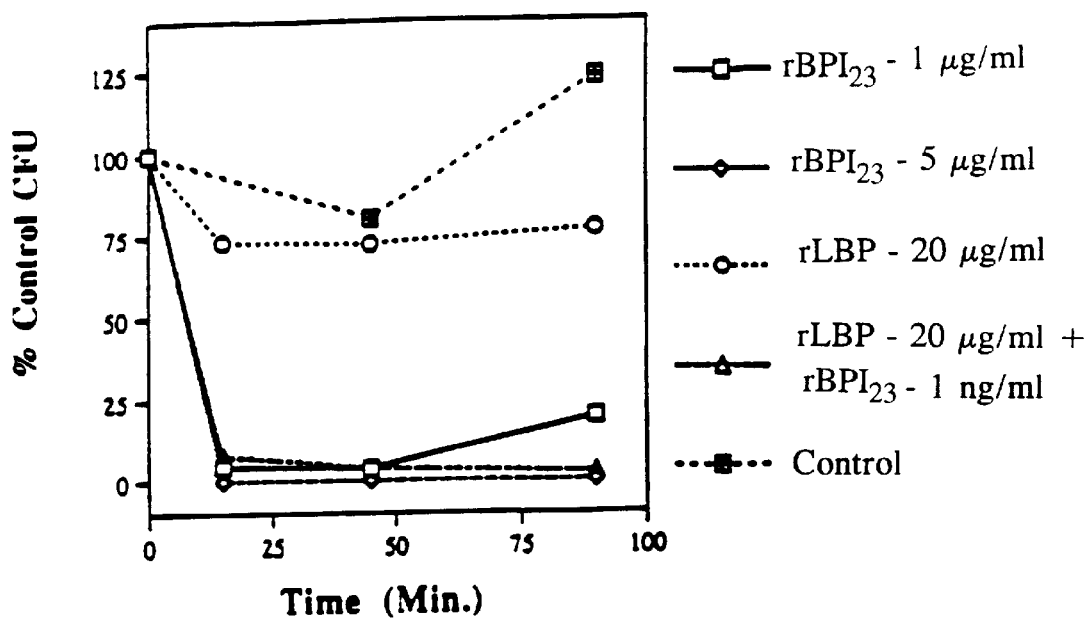
FIGS. 18a and 18b depict the results of plate growth bactericidal assays with rLBP, $rBPI_{23}$ and combinations thereof in the presence and absence of BSA.
Figure 18B:
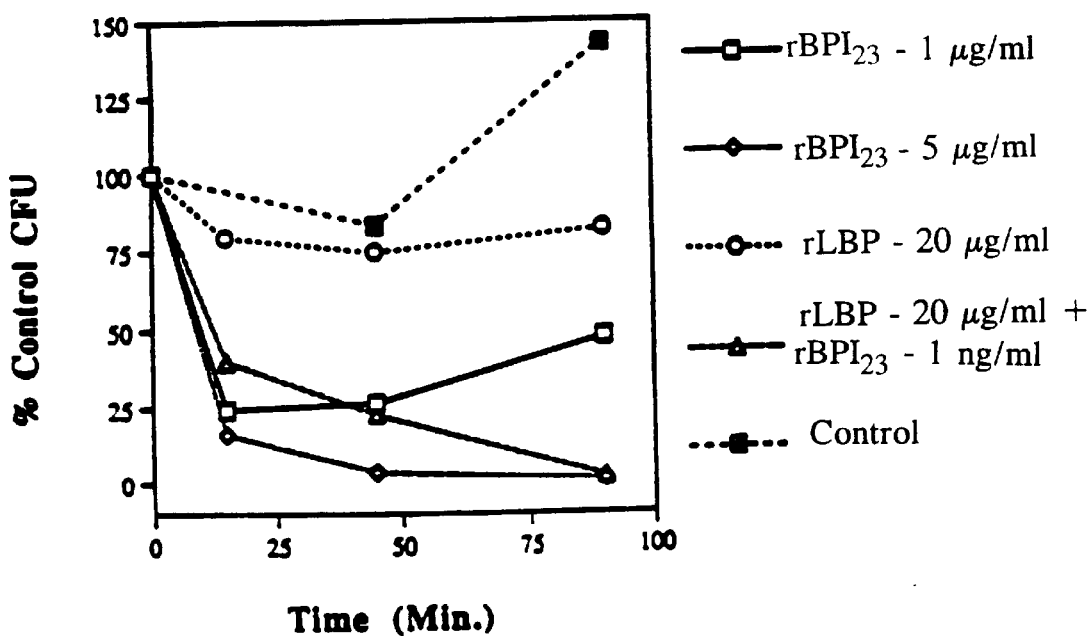

Effect of BSA on LBP Potentiation of BPI Bactericidal Activity in a Plate Assay In this example the effect of BSA on potentiation by LBP of the bactericidal effect of rBPI$_{23}$ protein was determined in a plate assay. It is noted that experiments reported by Ooi et al., *J. Biol. Chem.*, 265:15956 (1990) showed that potentiation of BPI by p15 did not occur when cells were plated on BSA supplemented nutrient agar. According to this example, *E. coli* J5 cells at a concentration of $4\times10^7$ cells/mL in 200 μl of buffered salts solution were incubated with rBPI$_{23}$ at concentrations of 1 and 5 μg/mL and with rLBP at 20 μg/mL with and without rBPI$_{23}$ at 1 ng/mL for 15, 45 and 90 minutes at 37° C., diluted in physiological saline and were plated onto agar plates supplemented with 0.1% BSA or unsupplemented control plates. The results are shown in FIGS. 18*a* and 18*b*. In FIGS. 18*a* and 18*b* with the data depicted as follows: rBPI$_{23}$ at 1 μg/mL, —□—; rBPI$_{23}$ at 5 μg/mL, —◇—; rLBP at 20 μg/mL, —○—; 20 μg/mL rLBP with 1 ng/mL rBPI$_{23}$, —△—; and the squares containing the crosses represent controls.

The results in FIGS. 18*a* (control: without BSA) or 18*b* (with BSA) show that BPI protein alone at 5 μg/mL (in the presence of BSA) results in about 95% cell killing by 45 minutes while BPI protein at 1 μg/mL, which is sufficient in the absence of BSA to achieve cell killing of 95% at 45 minutes, never achieved higher than about 75% killing when plated on BSA supplemented agar. By comparison, the combination of rLBP and rBPI23 resulted in approximately 95% cell killing by 90 minutes. Thus, LBP potentiated the irreversible bactericidal effect of rBPI$_{23}$ at a concentration of 1 ng/mL BPI. The incubation of cells with rLBP alone only caused a slight (25%) reduction in CFU relative to the control, although there did not seem to be evidence of cell division by 90 minutes with these cells as there was in the buffer-treated control. The results for plating on the BSA-supplemented nutrient agar, demonstrated that LBP potentiates the late, irreversible stage of BPI action. It is noted that while the LBP/BPI protein combination ultimately achieved the same degree of killing as rBPI$_{23}$ alone at 5 μg/mL (approximately 98%), it took longer to reach this level, requiring about 90 minutes versus 45 minutes for the BPI protein alone. This suggests that the cell killing kinetics for the LBP-potentiated BPI may be slower than for rBPI alone.

EXAMPLE 6

LBP Protein product Potentiation of BPI Protein Product Bactericidal Activity in a Plate Assay

Figure 19:
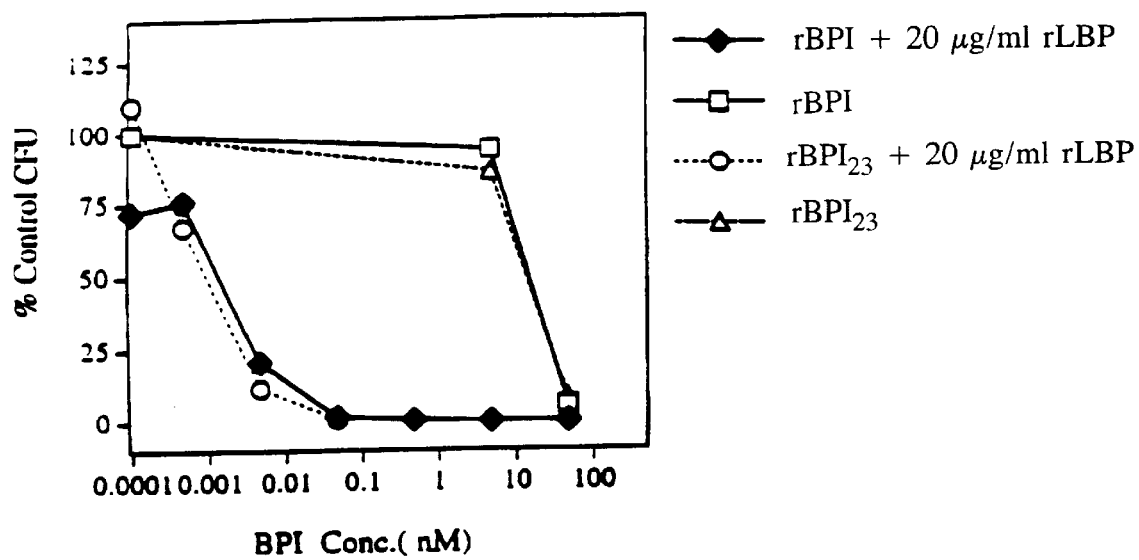
FIG. 19 depicts the results of a plate growth bactericidal assay with rBPI, $rBPI_{23}$, rLBP and combinations thereof.
Figure 20:
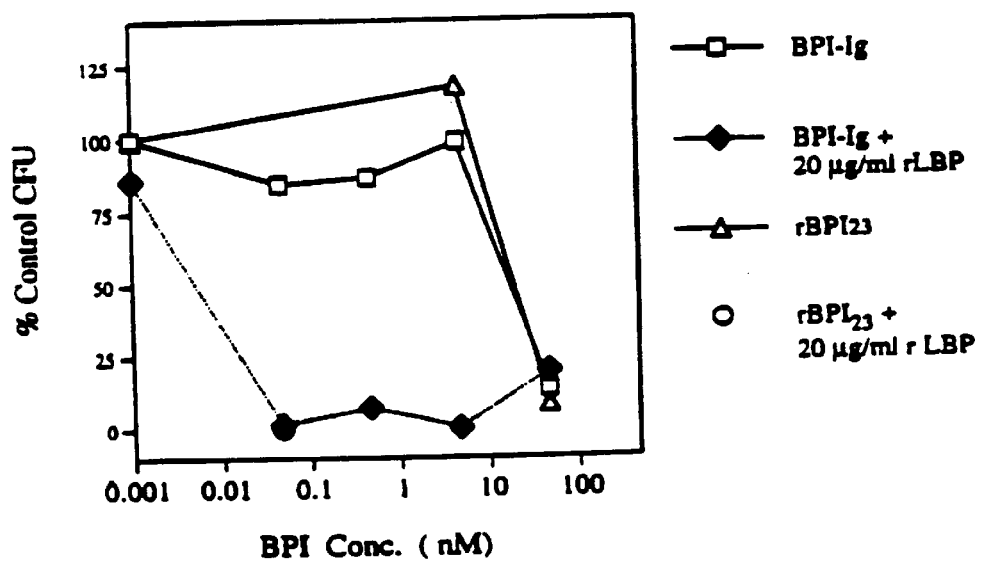
FIG. 20 depicts the results of a plate growth bactericidal assay with a recombinant BPI-Ig fusion protein [BPI-191/Hinge-$CH_2CH_3$], $rBPI_{23}$ rLBP and combinations thereof.
Figure 21:
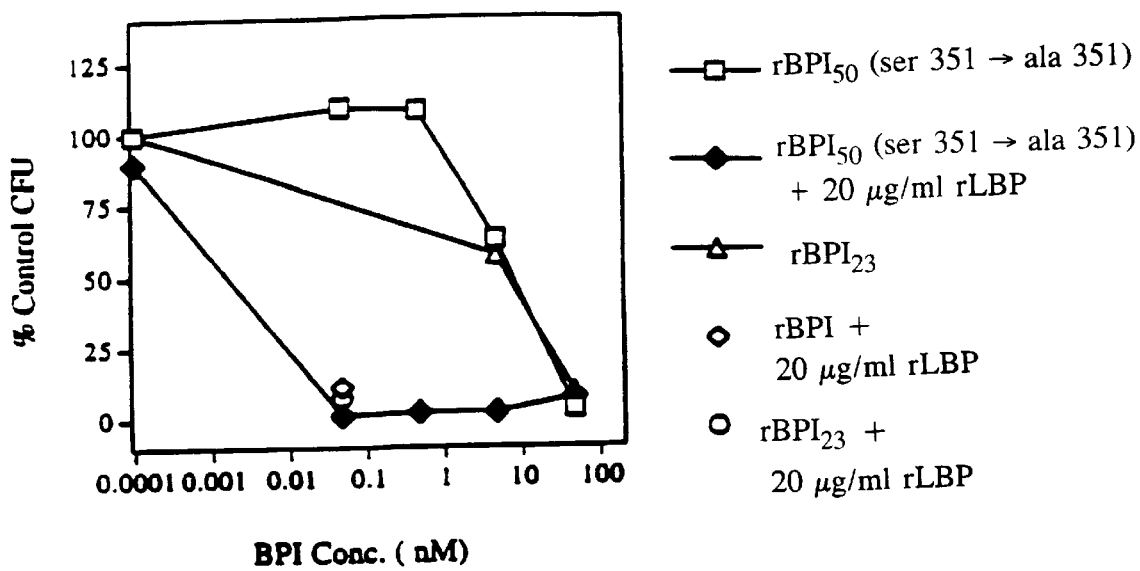
FIG. 21 depicts the results of a plate growth bactericidal assay with $rBPI_{50}$ (ser 351 ala 351), $rBPI_{23}$, rBPI rLBP and combinations thereof.
Figure 22:
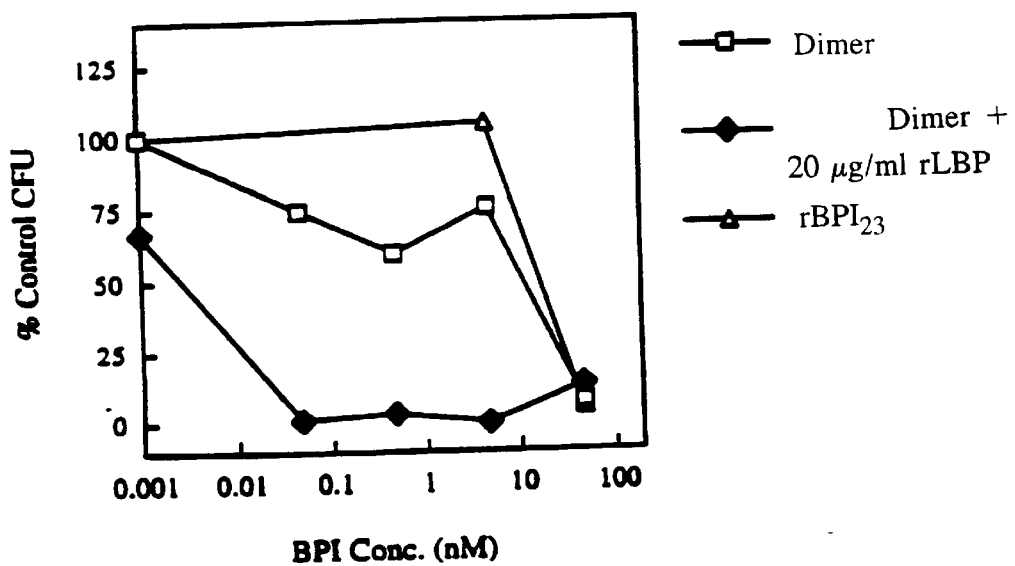
FIG. 22 depicts the results of a plate growth bactericidal assay with a recombinant dimeric form of an N-terminal BPI fragment (BPI dimer)
Figure 23A:
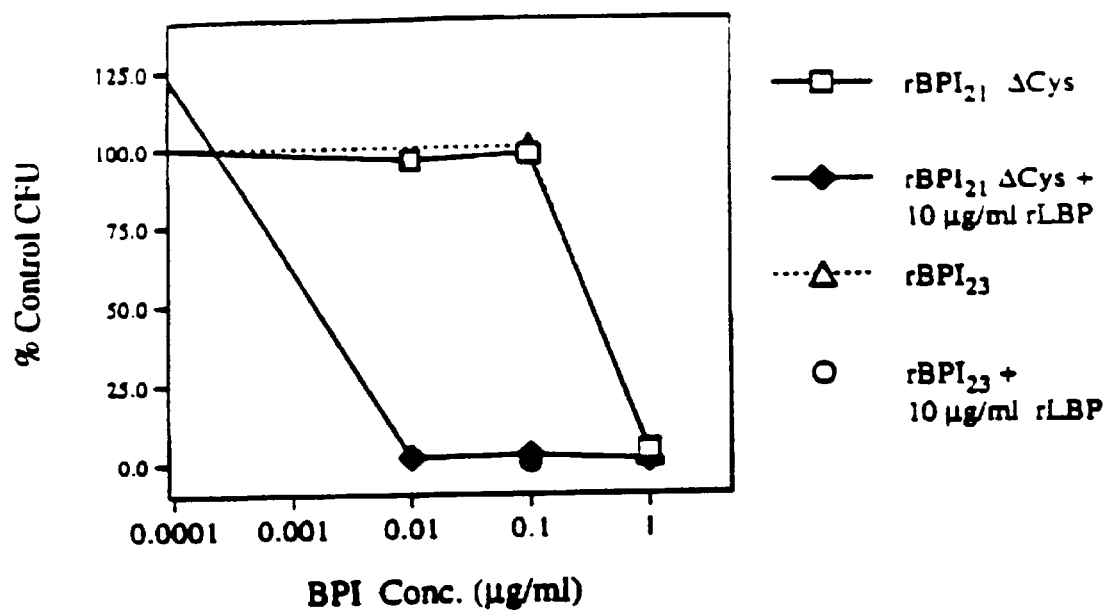
FIGS. 23a and b depicts the results of a plate growth bactericidal assay with $rBPI_{21}\Delta cys$, $rBPI_{23}$ rLBP and combinations thereof.
Figure 23B:
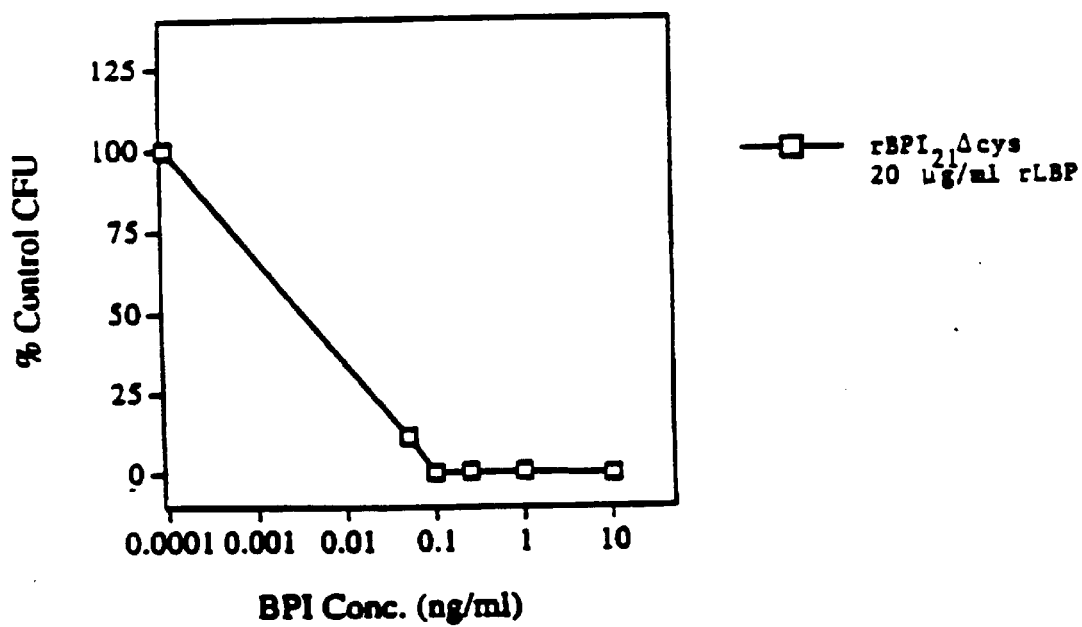

*E. coli* plate growth bactericidal assays as described in Example 2 were conducted utilizing rLBP with a variety of BPI protein products including a recombinant BPI holoprotein [rBPI$_{50}$], a recombinant N-terminal fragment of BPI [rBPI$_{23}$], a recombinant BPI-Ig fusion protein [BPI-191/Hinge-CH$_2$CH$_3$], a recombinant variant of BPI holoprotein in which a single glycosylation site has been changed (ser 351→ala 351), a recombinant dimeric form of an N-terminal BPI fragment, and a recombinant analog of an N-terminal BPI fragment in which a cysteine residue has been changed (cys 132→ala 132) rBPI$_{21}$Δcys with the results shown in FIGS. 19 through 23 below. FIG. 19 shows the results with recombinant rBPI holoprotein, rBPI. In FIG. 19, the data depicted as follows: rBPI with 20 μg/mL rLBP, —◆—; rBPI alone, —□—; rBPI$_{23}$ with 20 μg/mL rLBP, —○—; and rBPI$_{23}$ alone, —△—. FIGS. 19, 20 and 21 show the results with a recombinant N-terminal fragment of BPI, rBPI$_{23}$. FIG. 20 shows the results with a recombinant BPI-Ig fusion protein comprising N-terminal BPI (1–191) and the hinge, CH$_2$ and CH$_3$ constant domains of an immunoglobulin heavy chain according to U.S. patent application Ser. No. 08/064,693 filed May 19, 1993 which is a continuation-in-part of U.S. patent application No. 07/885,911 filed May 19, 1992 and referred to in the specification of the pending application. In FIG. 20 the data are depicted as follows: BPI-Ig fusion protein product alone, —□—; the BPI-Ig fusion protein product with 20 μg/mL rLBP, —◆—; rBPI$_{23}$ alone, —△—; and rBPI$_{23}$ with 20 μg/mL rLBP, —○—. FIG. 21 shows the results with a recombinant variant of BPI holoprotein in which a single glycosylation site has been removed (ser 351→ala 351). In FIG. 21 the data are depicted as follows: rBPI$_{50}$ (ser 351→ala 351) alone, —□—; rBPI$_{50}$ (ser 351→ala 351) with 20 μg/mL rLBP, —◆—; rBPI$_{23}$, —△—; rBPI with 20 μg/mL rLBP, ◇; and rBPI$_{23}$ with 20 μg/mL rLBP, ○. FIG. 22 shows the results with a recombinant dimeric form of an N-terminal BPI fragment produced according to the methods of U.S. patent application Ser. No. 08/212,132 filed Mar. 11, 1994. In FIG. 22 the data are depicted as follows: BPI dimer, —□—; BPI dimer with 20 μg/mL rLBP, —◆—; and rBPI$_{23}$, —△—. FIGS. 23*a* and *b* show the results with a recombinant analog of an N-terminal BPI fragment (in which a cysteine residue has been changed (cys 132→ala 132), rBPI$_{21}$Δcys, which is described in co-owned, copending U.S. patent application Ser. No. 08/013,801 filed Feb. 2, 1993. In FIG. 23*a* the data are depicted as follows: rBPI$_{21}$Δcys alone, —□—; rBPI$_{21}$Δcys with 10 μg/mL rLBP, —◆—; rBPI$_{23}$ alone, —△—; and rBPI$_{23}$ with 10 μg/mL rLBP, ○. In FIG. 23*b,* the data are depicted as follows: rBPI$_{21}$Δcys with 20 μg/mL rLBP, —□—. These results demonstrate that the bactericidal properties of each of the exemplified BPI protein products are potentiated by the addition of rLBP.

EXAMPLE 7

LBP Potentiation of BPI Permeabilization Activity with Actinomycin D

The effect of LBP proteins on the permeability increasing properties of BPI was determined. *E. coli* J5 bacteria were grown overnight in TYE broth and then a 1/200 dilution was subcultured in TEA medium. Bacteria were harvested at mid-logarithmic phase, suspended at about $8\times10^8$ cells/mL in sterile physiological saline and diluted 20-fold in a bactericidal assay medium consisting of 10% Hanks' balanced salts solution, 40 mM Tris-HCl (pH 7.4), 0.1% casamino acids, 0.9% NaCl and 0.4 mg/mL BSA (final cell density, about $4\times10^7$ cells/mL). Cells at about $4\times10^7$ cells/mL were mixed in a total volume of 200 µL with various concentrations of rBPI$_{23}$ with or without 20 µg/mL rLBP followed by 50 µg/mL actinomycin D (Sigma). As a control, the same experiment was performed without the actinomycin D. Following a 10 minute incubation at 37° C., the cells were diluted in sterile physiological saline containing 4 mg/mL BSA and plated on nutrient agar containing 0.9% NaCl and 1 mg/mL BSA.

Figure 24:
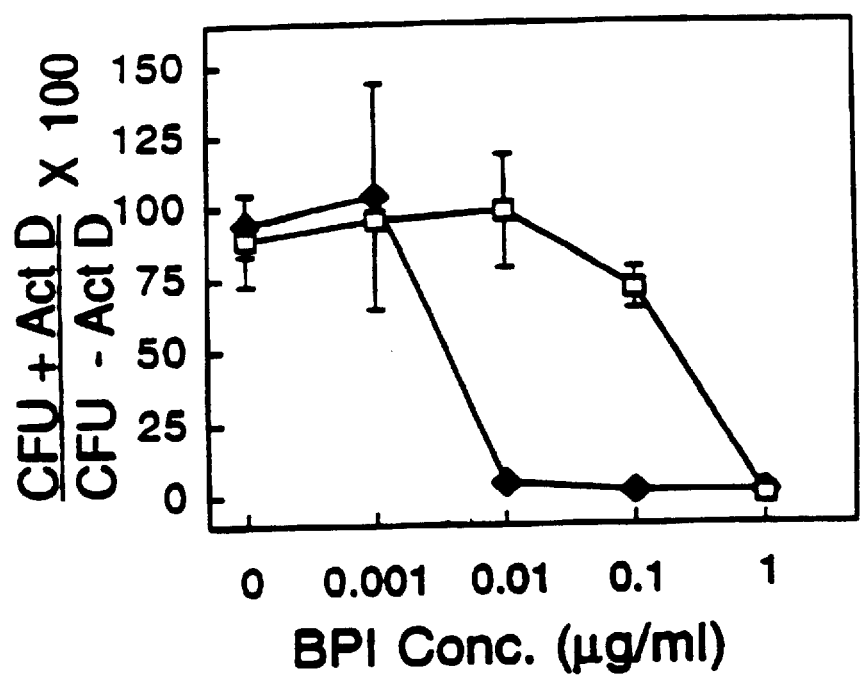
FIG. 24 depicts the results of Actinomycin D permeability assays utilizing $rBPI_{23}$, with and without rLBP.

The results are shown in FIG. 24 show that under these conditions, cells are protected by serum albumin from direct effects of BPI but not from the combined effects of BPI plus actinomycin D. In FIG. 24 Actinomycin D—assisted killing was the ratio of (CFU+ActD/CFU—ActD)×100 determined for each concentration in the assay. The results represent an average of three separate experiments with rBPI$_{23}$ alone, (—□—); rLBP plus rBPI$_{23}$, (—♦—). Treatment of cells with 1 µg/mL of rBPI$_{23}$ plus actinomycin D caused a reduction in CFUs of >95% on serum albumin-supplemented agar relative to treatment with rBPI$_{23}$ alone. Lower concentrations of rBPI$_{23}$ did not substantially facilitate actinomycin D-assisted killing and actinomycin D alone was not bactericidal in this assay. Addition of 20 µg/mL rLBP reduced by almost 100-fold the rBPI$_{23}$ concentration required to achieve approximately 95% actinomycin D-assisted killing, though rLBP alone did not permeabilize cells to actinomycin D. These results confirm that rLBP also potentiates the initial stage of rBPI$_{23}$ activity.

EXAMPLE 8

LBP Potentiation of BPI Activity in a Protein Synthesis Assay

Figure 25A:
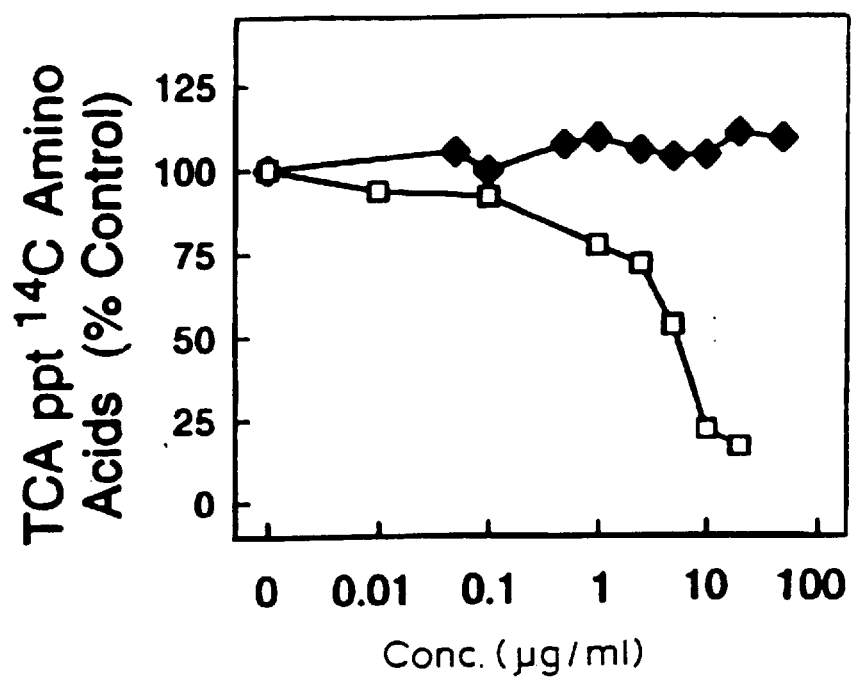
FIGS. 25a and b depict the results of rLBP and rBPI$_{23}$ in a protein synthesis assay.
Figure 25B:
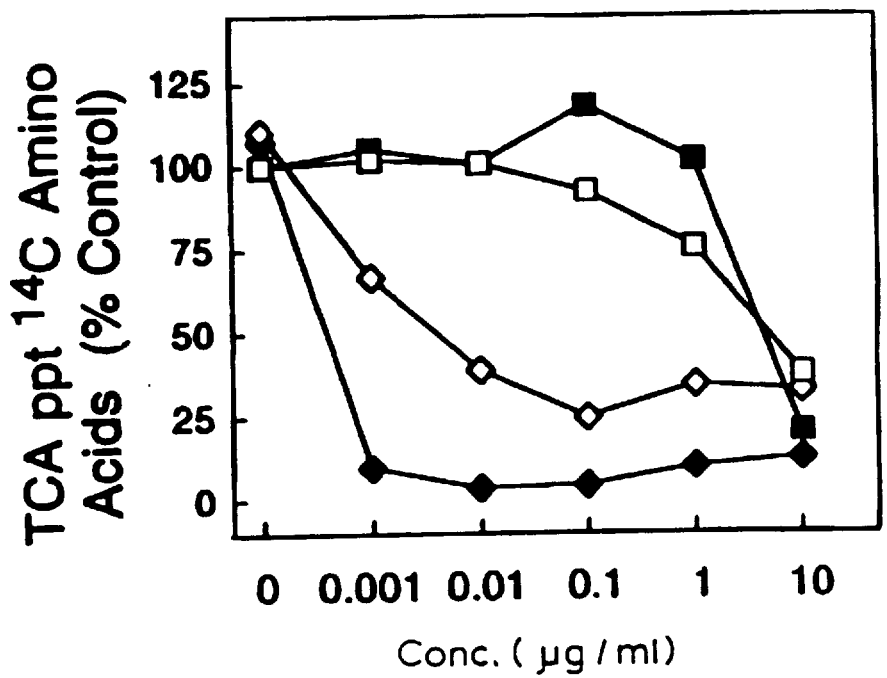

The effect of BPI and LBP on protein synthesis was assessed for *E. coli* J5 cells. The bacteria cells were grown overnight in TYE broth and then a 1/200 dilution was subcultured in TEA medium. Bacteria were harvested at mid-logarithmic phase, suspended at about $8\times10^8$ cells/mL in sterile physiological saline and diluted 20-fold in a bactericidal assay medium consisting of 10% Hanks' balanced salts solution, 40 mM Tris-HCl (pH 7.4), 0.1% casamino acids, and 0.9% NaCl (final cell density, about $4\times10^7$ cells/mL). The cells were incubated at 37° C. for 45 or 90 minutes with rBPI$_{23}$, rLBP or rBPI$_{23}$ plus rLBP in the bactericidal assay medium before 0.4 µCi of $^{14}$C-amino acids (New England Nuclear, Boston, Mass.) was added and incubation was continued for an additional 20 minutes at 37° C. Incorporation of the $^{14}$C-amino acids was linear as a function of time for at least 20 minutes. Cells were treated with 3 mL of cold 10% trichloroacetic acid to arrest protein synthesis and release free $^{14}$C-amino acids from cells which were then applied to a 0.45 µM HA Millipore filter, washed once with 3 mL 10% trichloroacetic acid and then with 5 mL water. The filters were dried and counted in 10 mL of scintillation cocktail (Ready Flow III®, Beckman Instruments, Fullerton, Calif.) in a Beckman 7500® scintillation counter with the results shown in FIGS. 25a and 25b. In FIG. 25a the effect of rBPI$_{23}$ (—□—) and rLBP (—♦—) alone on protein synthesis is shown. In FIG. 25b the effect of treatment with rBPI$_{23}$ alone (—■— and —□—, with the —□— representing treatment for 45 minutes and the —■— representing treatment for 90 minutes), and rLBP at 20 µl/mL plus rBPI$_{23}$ (—◊— and —♦—, with the —◊— representing treatment for 45 minutes and the —♦— representing treatment for 90 minutes) is shown.

These results show that treatment with BPI ultimately leads to impairment of protein synthesis as measured by incorporation of radiolabeled amino acids into an acid precipitable, cell-associated state. The results demonstrate that while rLBP alone at concentrations up to 50 µg/mL had no effect on protein synthesis (FIG. 25a), rLBP at 20 µg/mL enhanced rBPI$_{23}$ mediated inhibition of protein synthesis by about 1000-fold following a 45 minute incubation and 10,000-fold following a 90 minute incubation (FIG. 25b).

EXAMPLE 9

Potentiation of BPI Bactericidal Activity by an LBP/BPI Hybrid in a Plate Assay

The effect of an LBP/BPI hybrid molecule on the bactericidal effect of rBPI$_{23}$ in a plate assay was determined. A plasmid encoding the LBP(1–197)BPI(200–456) hybrid was constructed by combining appropriate portions of the two molecules via a ClaI restriction site engineered into homologous locations in the DNA encoding the two molecules. The first step necessary for the construction of the mammalian expression vector pING4160 was the construction of two intermediate plasmids to introduce a ClaI restriction site by overlap extension PCR mutagenesis at the Ile-Asp at positions 197–198 in LBP (to generate plasmid pML127) and the Ile-Asp at positions 199–200 in BPI (to generate plasmid pML126). These were silent mutations which changed the nucleotide sequence only and not the amino acid sequence. The next step was to combine the amino terminal portion of LBP from pML127 with the carboxyl terminal of BPI from pML126 at the homologous ClaI sites to generate the intermediate plasmid pML128. The final step was then to subclone the LBP-BPI insert from pML126 into a mammalian expression vector to generate pING4160.

To construct plasmid pML127 (LBP with ClaI at 197–198), overlapping primers were designed to incorporate the changes necessary to encode a ClaI recognition site at the desired location. The template was pML125, a plasmid containing an insert encoding full length LBP. The primers were LBP-10, SEQ. ID. NO: 7, and LBP-8, SEQ. ID. NO: 8 facing downstream, and LBP-11, SEQ. ID. NO: 9 and LBP-Bsm, SEQ. ID. NO: 10 facing upstream. Two separate PCR reactions were carried out with primer pairs LBP-Bsm and LBP-11, to generate a 600 bp fragment that was then digested with StuI and ClaI to generate a 389 bp fragment, and primer pairs LBP-10 and LBP-8, to generate a 328 bp fragment that was then digested with ClaI and Bsu36I to generate a 148 bp fragment. The two resulting fragments were then ligated to the Bsu36I-StuI vector fragment from pML125 to generate the plasmid pML127.

To construct plasmid pML126 (BPI with ClaI at 199–200), overlapping primers were designed to incorporate the changes necessary to encode a ClaI recognition site at the desired location. The template was pML124, a plasmid containing an insert encoding full length BPI. The primers were BPI-63, SEQ. ID. NO: 11 and BPI-7, SEQ. ID. NO: 12 facing downstream, and BPI-64, SEQ. ID. NO: 13, and BPI-40, SEQ. ID. NO: 14, facing upstream. Two separate PCR reactions were carried out with primer pairs BPI-40 and BPI-64, to generate a 260 bp fragment that was then digested with PmlI and ClaI to generate a 170 bp fragment, and primer pairs BPI-7 and BPI-63, to generate a 296 bp fragment that was then digested with ClaI and BstXI to generate a 215 bp fragment. The two resulting fragments were then ligated to the BstXI-PmlI vector fragment from pML124 to generate the plasmid pML126.

To construct pML128, the intermediate plasmid encoding the LBP(1–197)BPI(200–456) hybrid, the 620 bp HindIII- ClaI fragment encoding the amino terminal region of BPI in the plasmid pML126 was replaced with the corresponding HindIII-ClaI fragment from pML127 encoding the amino terminal region of LBP.

To construct the mammalian expression vector pING4160, the 623 bp FspI-Bsu36I fragment of pML128 was ligated to the 361 bp SalI-FspI fragment from pING4539, (described in Gazzano-Santaro et al., U.S. application Ser. No. 08/261,660 filed Jun. 17, 1994) which includes the LBP signal sequence, and the approximately 8630 bp Bsu36I-SalI fragment from pING4321. The latter fragment includes sequences encoding part of the carboxyl terminus of BPI and all the vector sequences, which include the CMV promoter and the light chain 3' transcription termination sequences (as described in Ammons et al., U.S. application Ser. No. 08/212,132, filed Mar. 11, 1994).

To obtain the protein, beads co-cultured with CHO-K1 cells transfected with pING 4160 were washed with approximately 600 mls of 20 mM sodium acetate, pH 4.0 mM NaCl and then 600 mls of the same buffer containing 600 mM NaCl. Protein was eluted in two steps of 20 mM sodium acetate; the first with 1.0M NaCl and the second with 1.5M NaCl, with the majority of the desired protein eluting from the S-Sepharose in the 1.0M step. Fractions containing the protein were then pooled and diluted to a final NaCl concentration of 300 mM with the addition of MES buffer, to a final concentration of 20 mM MES, pH 5.0. The diluted material recovered from all cell harvests was combined, yielding a final volume of approximately 6.5 liters. This pooled eluate was applied to two columns arranged in a tandem fashion, the first being a 100 ml Q-Sepharose column and the second a 12 ml CM-Spherodex column. The flow through material, which contained the desired protein, was adjusted to pH 4.0 and loaded in three batches on to a 15 ml S-Sepharose column. Each time the column was washed with 20 mM MES, pH 4.0 200 mM NaCl and the bound protein recovered with a step elution of 20 mM MES, pH 5.5, 1.2M NaCl. The volume of the recovered protein was approximately 40 mls. This material was then run on a S-100 size exclusion column in 5 mM sodium citrate, pH 5.0, 150 mM NaCl. Column fractions were assayed using Coommassie stained SDS-PAGE and Western analysis using an anti-LBP primary antibody. P4160 fractions containing the protein LBP (1–197)BPI(200–456).

Figure 26:
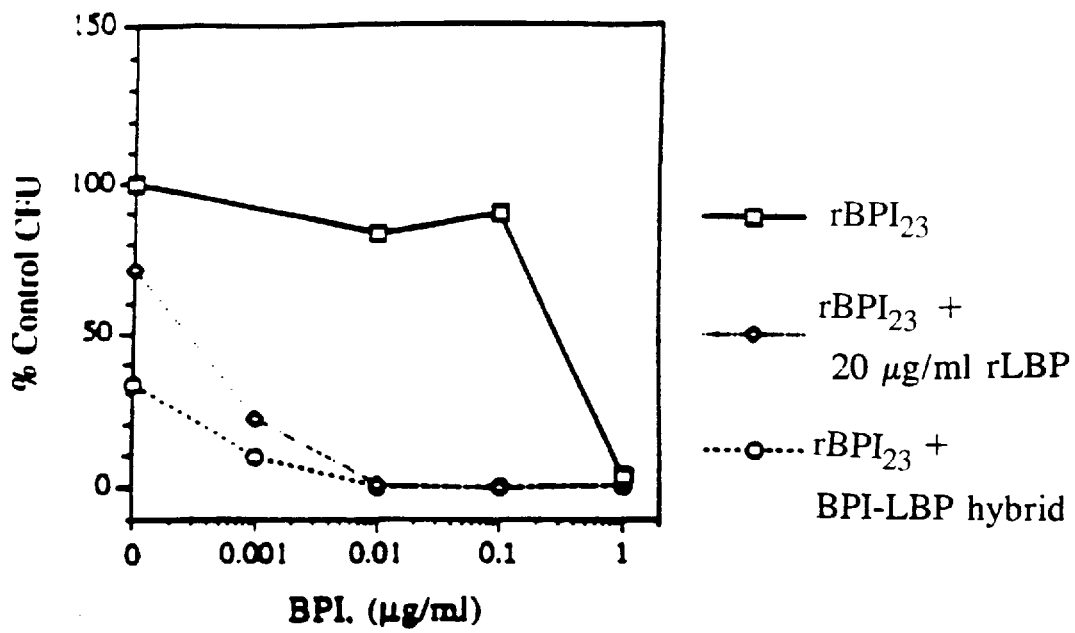
FIG. 26 depicts the results of a plate growth bactericidal assay with rBPI$_{23}$ in combination with either rLBP or an LBP/BPI hybrid protein (LBP(1–197)/BPI(200–456)

Specifically, an *E. coli* plate growth assay was carried out according to the general method of Example 2 using rBPI$_{23}$, rBPI$_{23}$ in combination with 20 μg/mL rLBP, and rBPI$_{23}$ in combination with 20 μg/mL of an LBP/BPI hybrid designated LBP(1–197)/BPI(200–456) comprising the first 197 residues of LBP linked to amino acid residues 200–456 of BPI. The results illustrated in FIG. 26 wherein the results with rBPI$_{23}$ alone are depicted by —□—, the results with rBPI$_{23}$ in combination with 20 μg/mL rLBP are depicted by —◊—, and the results with rBPI$_{23}$ in combination with 20 μg/mL LBP/BPI hybrid are depicted by —○— show that both rLBP and the LBP/BPI hybrid potentiate the bactericidal effect of rBPI$_{23}$.

EXAMPLE 10

Effect of Order of Addition of BPI and LBP in a Plate Bactericidal Assay

The effect of order of addition of BPI and LBP protein products in a plate bactericidal assay was determined by varying the order of addition of the protein products and incubating cells in the presence of only one of the protein products prior to contacting with the second protein product. Specifically *E. coli* J5 cells were grown up according to the method of Example 2 and the bactericidal assays were conducted according to the methods of that example. rBPI$_{23}$ was used at a concentration of 1 ng/mL while rLBP was administered at 20 μg/mL. According to the "normal" condition such as practiced in Example 2 above, one of the protein products was added and was followed by the other protein product within the first 2–3 minutes. Alternatively, one of the protein products was added to the cells which were allowed to incubate for 15 or 40 minutes prior to addition of the other protein product. The total incubation time was 45 minutes for all samples, thus the incubation period with both the BPI and LBP protein products present was 45, 30 or 5 minutes.

Figure 27:
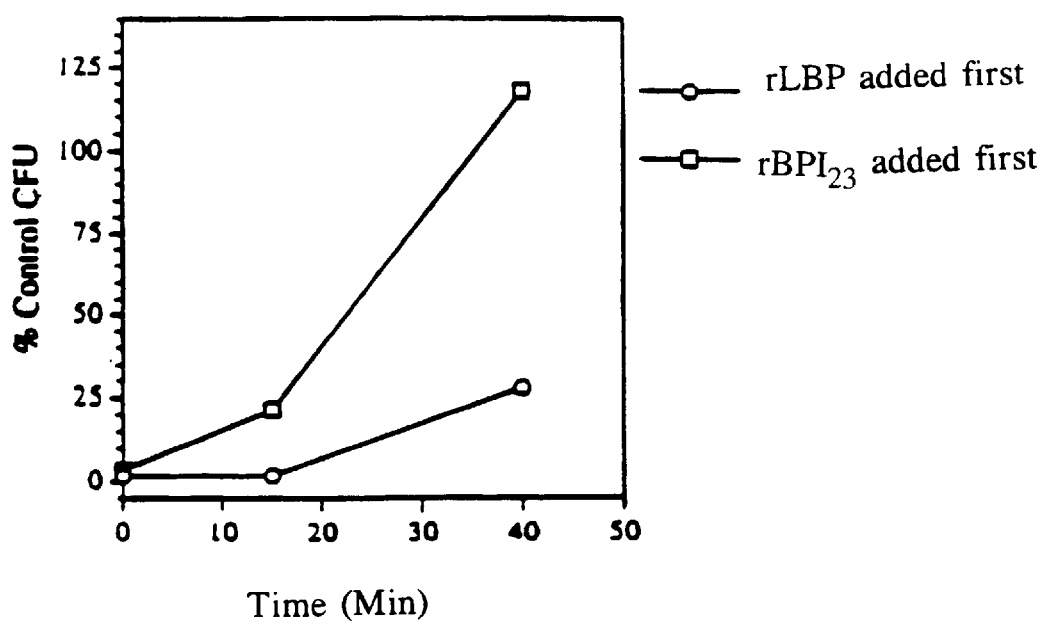
FIG. 27 depicts the results of a plate growth bactericidal assay examining the effect of order of addition of rBPI$_{23}$ and rLBP on potentiation of BPI bactericidal activity.

The results are shown in FIG. 27 wherein the experiments in which rLBP was added first are depicted by (—○—) and the experiments in which rBPI$_{23}$ was added first are depicted by (—□—) with the results at time 0 being those experiments in which both protein products were added essentially simultaneously. These results suggest that pre-treatment of cells with LBP protein products sensitize them to bactericidal action by a small number of BPI molecules even if the BPI protein product is added to the cells 15 or 40 minutes after the LBP protein product. In contrast, pre-treatment with a low concentration of a BPI protein product is progressively less effective as a function of time. For example, a 40 minute pretreatment with rBPI$_{23}$ followed by a 5 minute incubation with rLBP results in no bactericidal effect.

Without being bound by a theory of action, it is noted that these results are consistent with the model whereby LBP protein products function by occupying the large number of available LPS sites on the outer membrane surface that are normally bound by the majority of BPI molecules. Binding of LBP (or an excess of BPI) to these sites could promote subsequent interaction of a small number of BPI molecules at a second class of sites at or below the outer membrane surface leading ultimately to growth arrest and cell death. Such a model might suggest that addition of low concentrations of BPI first could cause interaction of BPI at sites that do not result in lethal action. Incubation with LBP first, however, would provide full occupancy of these sites allowing BPI to interact with sites leading to lethal action.

Numerous modifications and variations in the practice of the invention are expected to occur to those skilled in the art upon consideration of the foregoing description of the presently preferred embodiments thereof. Consequently, the only limitations which should be placed upon the scope of the present invention are those which appear in the appended claims.

What is claimed is:

1. A method of treating a gram-negative bacterial infection in a subject comprising administering a bactericidal/permeability-increasing protein (BPI) protein product and a lipopolysaccharide binding protein (LBP) protein product, to said subject in amounts effective to treat the gram-negative bacterial infection.

2. The method of claim 1 wherein the LBP protein product is administered in an amount effective to potentiate the bactericidal properties of said BPI protein product.

3. The method of claim 1 wherein the LBP protein product is an amino-terminal LBP fragment.

4. The method of claim 1 wherein the LBP protein product is characterized by a molecular weight of about 25 kD.

5. The method of claim 1 wherein the LBP protein product is rLBP.

6. The method of claim 1 wherein the proteins are administered systemically.

7. The method of claim 1 wherein the proteins are administered topically.

8. A method of killing gram-negative bacteria comprising administering to said bacteria a BPI protein product in combination with an LBP protein product in an amount effective to potentiate the bactericidal properties of said BPI protein product.

9. The method of claim 8 wherein said BPI protein product and said LBP protein product are administered in vivo.

10. The method of claim 8 wherein said BPI protein product and said LBP protein product are administered in vitro.

11. The method of claim 8 wherein the LBP protein product is an amino-terminal LBP fragment.

12. The method of claim 8 wherein the LBP protein product is characterized by a molecular weight of about 25 kD.

13. The method of claim 8 wherein the LBP protein product is LBP.

14. A pharmaceutical composition for treatment of gram-negative bacterial infection comprising a BPI protein product and an LBP protein product in an amount effective to potentiate the bactericidal properties of said BPI protein product.

15. The pharmaceutical composition of claim 14 comprising a pharmaceutically-acceptable diluent, adjuvant, or carrier.

16. The pharmaceutical composition of claim 14 wherein the LBP protein product is an amino-terminal LBP fragment.

17. The pharmaceutical composition of claim 14 wherein the LBP protein product is characterized by a molecular weight of about 25 kD.

18. A gram-negative cytotoxic composition comprising a BPI protein product and an LBP protein product in an amount effective to potentiate the bactericidal properties of said BPI protein product.

19. The method of claim 1 wherein the LBP protein product is LBP(1–197)/BPI(200–456) hybrid.

20. The method of claim 8 wherein the LBP protein product is LBP(1–197)/BPI(200–456) hybrid.

21. The pharmaceutical composition of claim 14 wherein the LBP protein product is LBP(1–197)/BPI(200–456) hybrid.

* * * * *

UNITED STATES PATENT AND TRADEMARK OFFICE
CERTIFICATE OF CORRECTION

PATENT NO.     : 5,770,561
DATED          : June 23, 1998
INVENTOR(S)    : Arnold Horwitz It is certified that error appears in the above-identified patent and that said Letters Patent is hereby corrected as shown below:

<u>Title page,</u>
Item [56], OTHER PUBLICATIONS,
Replace "Bactericidal, Permeability" with -- Bactericidal/Permeability --.

<u>Column 4,</u>
Line 5, replace "rBPI23" with -- rBPI$_{23}$ --.
Line 55, replace "[BPI-191" with -- [BPI-191/ --.

<u>Column 8,</u>
Line 37, replace "rBPI21Δcys" with -- rBPI$_{21}$Δcys --.

<u>Column 9,</u>
Line 10, replace "rLBP2$_5$" with -- rLBP$_{25}$ --.

<u>Column 11,</u>
Line 29, replace "- ◊ - and" with -- - ◊ - ; and --.

<u>Column 12,</u>
Line 40, replace "50 g/mL" with -- 50 µg/mL --.

<u>Column 13,</u>
Line 52, replace "rBPI23" with -- rBPI$_{23}$ --.

Signed and Sealed this

First Day of October, 2002

Attest:

Attesting Officer

JAMES E. ROGAN
*Director of the United States Patent and Trademark Office*